US005646254A

United States Patent [19]

Johnson et al.

[11] Patent Number: 5,646,254

[45] Date of Patent: Jul. 8, 1997

[54] ANTIBODIES FOR HUMAN PHOSPHOLIPASE INHIBITORY PROTEIN (HPIP)

[75] Inventors: Lorin K. Johnson, Pleasanton; John P. Longenecker, Mountain View, both of Calif.

[73] Assignee: Scios Nova Inc., Mountain View, Calif.

[21] Appl. No.: 233,464

[22] Filed: Apr. 26, 1994

Related U.S. Application Data

[62] Division of Ser. No. 115,316, Sep. 1, 1993, Pat. No. 5,342,764, which is a division of Ser. No. 871,577, Apr. 20, 1992, Pat. No. 5,264,550, which is a continuation of Ser. No. 538,692, Jun. 14, 1990, abandoned, which is a continuation of Ser. No. 883,598, Jul. 9, 1986, abandoned, which is a continuation-in-part of Ser. No. 723,046, Apr. 15, 1985, abandoned.

[51] Int. Cl.$^{6}$ .......................... C07K 16/00; C07K 16/40

[52] U.S. Cl. .............................. 530/388.85; 530/388.26; 530/389.1; 530/387.1

[58] Field of Search ............................ 424/142.1, 145.1, 424/537, 130.1; 530/350, 395, 851, 388.26, 388.85, 389.1, 387.1

[56] References Cited

U.S. PATENT DOCUMENTS 5,264,550 11/1993 Johnson et al. .

OTHER PUBLICATIONS

Hong et al., "Inhibition of arachidonic acid release from cells as the biochemical action of anti-inflammatory corticosteroids" *Proc. Natl. Acad. Sci. USA* (1976) 73(5):1730–1734.

Hirata, F., "The regulation of lipomodulin, a phospholipase inhibitory protein, in rabbit neutrophils by phosphorylation" *J. Biol. Chem.* (1981) 256(15):7730–7733.

Blackwell et al., "Macrocortin: a polypeptide causing the anti-phospholipase effect of glucocorticoids" *Nature* (1980) 287:147–149.

Russo-Marie et al., "Dexamethasone-induced inhibition of prostaglandin production does not result from a direct action on phospholipase activities but is mediated through a steroid-inducible factor" *Biochim. Biophys. Acta* (1982) 712:177–185.

Hirata et al., "A phospholipase $A_2$ inhibitory protein in rabbit neutrophils induced by glucocorticoids" *Proc. Natl. Acad. Sci. USA* (1980) 77(5):2533–2536.

Rothhut et al., "Further characterization of the gucocorticoid-induced antiphospholipase protein renocortin" *Biochem. Biophys. Res. Commun.* (1983) 117(3):878–884.

Hirata et al., "Identification of several species of phospholipase inhibitory protein(s) by radioimmunoassay for lipomodulin" *Biochem. Biophys. Res. Commun.* (1982) 109(1):223–230.

Johnson et al., "Glucocorticoid action: a mechanism involving nuclear and non-nuclear pathways" *Brit. J. Dermatol.* (1982) 107(Suppl23):6–23.

Hattori et al., "Differentiation of a histiocytic lymphoma cell line by lipomodulin, a phospholipase inhibitory protein" *Biochem. Biophys. Res. Commun.* (1983) 111(2):551–559.

Errasfa et al., "The presence of lipocortin in human embryonic skin fibroblasts and its regulation by anti-inflammatory steroids" *Biochim. Biophys. Acta.* (1985) 847:247–254.

Wallner et al., "Cloning and expression of human lipocortin, a phospholipase $A_2$ inhibitor with potential anti-inflammatory activity" *Nature* (1986) 320:77–81.

Pepinski et al., "Purification and Partial sequence analysis of a 37-kDa protein that inhibits phospholipase $A_2$ activity from rat peritoneal exudates" *J. Biol. Chem.* (1986) 261:4239–4261.

*Primary Examiner*—Donald E. Adams
*Attorney, Agent, or Firm*—Morrison & Foerster

[57] ABSTRACT

Antibodies which react with the human phospholipase inhibitory protein/apolipoprotein AIV complex and hPIP are provided.

2 Claims, 19 Drawing Sheets

```
Linker
--------|                    ↓
GAA TTC CAC AAC AAC GAC ACC TTC CAC TTC CTG AAA TGC TGC AAC ACC    48
Glu Phe His Asn Asn Asp Thr Phe His Phe Leu Lys Cys Cys Asn Thr
 1               5                   10                  15
                            Intron
                 ↓          |.......>
ACC AAA|TGC AAC GAG GGC CCA|AGT AAG GAA CGG GAG ACA CAG GCA AGG    96
Thr Lys|Cys Asn Glu Gly Pro|Ser Lys Glu Arg Glu Thr Gln Ala Arg
              20                  25                  30
                                              PvuII
CCT GGG GTC GGG CAG GGG CAT GCA CTC AGG CAG ACA GCT GCG CAG TCA   144
Pro Gly Val Gly Gln Gly His Ala Leu Arg Gln Thr Ala Ala Gln Ser
         35                  40                  45

CTC TCT GGC AAT CAA GTC CTC TCT GGG TCT CTG TTT GCT TTT CTG AAA   192
Leu Ser Gly Asn Gln Val Leu Ser Gly Ser Leu Phe Ala Phe Leu Lys
     50                  55                  60

AAT GGG AGG GAA TTC                                               207
Asn Gly Arg Glu Phe
65
```

```
GAA TTC CTC ACC TTC CTG GAA TGC TGC AAC ACC ACC AAA TGC AAC GAG GGC CCA     54
            Thr Phe Leu Glu Cys Cys Asn Thr Thr Lys Cys Asn Glu Gly Pro
              1               5                  10                  15

ATC CTG GAG CTT GAA AAT CTG CCG CAG AAT GGC CGC CAG TGT TAC AGC TGC AAG    108
Ile Leu Glu Leu Glu Asn Leu Pro Gln Asn Gly Arg Gln Cys Tyr Ser Cys Lys
                 20                  25                  30

GGG AAC AGC ACC CAT GGA TGC TCC TCT GAA GAG ACT TTC CTC ATT GAC TGC CGA    162
Gly Asn Ser Thr His Gly Cys Ser Ser Glu Glu Thr Phe Leu Ile Asp Cys Arg
     35                  40                  45                  50

GGC CCC ATG AAT CAA TGT CTG GTA GCC ACC GGC ACT CAC GAA CGC TCA CTC TGG    216
Gly Pro MET Asn Gln Cys Leu Val Ala Thr Gly Thr His Glu Arg Ser Leu Trp
             55                  60                  → alternate exon

GGA AGC TGG TTG CCA TGT AAA AGT ACT ACT GCC CTG AGA CCA CCA TGC TGT GAG    270
Gly Ser Trp Leu Pro Cys Lys Ser Thr Thr Ala Leu Arg Pro Pro Cys Cys Glu
 70                  75                  80                  85

GAA GCC CAA GCT ACT CAT GTA TAA ATG CCA TGT GGA GAT AGA GCC CCA GAT GTT    324
Glu Ala Gln Ala Thr His Val
         90

TCA GCC ATC TCA GCC CAG GCA CCA GAC AAG TGG GTG AAG AAG CCA CCT TGG ACA    378

TGT AGC CCC AGC AGA TGT GAT ATA GAG AAG AAA CAG GAA ACT TGG CTA TAT TAG    432

TTT CCT AGG GCT GCC TGT GAT AAA TTA TTA CAA ACT TTA AAA AAA AAA ACT CGG    486

GGA GAG AAA TAG CAC ATT ATT TAC ATG ACT GGA CAA GGA CAG AAG GGG AAT TC     539
```

```
GGA ATT CCG GAT GAC CGC CAC CTC CGT GGC TGT GGC TAC CTT CCC GGC TGC CCG GGC TCC AAT    63
            Asp Asp Arg His Leu Arg Gly Cys Gly Tyr Leu Pro Gly Cys Pro Gly Ser Asn
              1               5                  10                  15

GGT TTC CAC AAC AAC GAC ACC TTC CAC TTC CTG AAA TGC TGC AAC ACC ACC AAA TGC AAC GAG   126
Gly Phe His Asn Asn Asp Thr Phe His Phe Leu Lys Cys Cys Asn Thr Thr Lys Cys Asn Glu
     20                  25                  30                  35

GGC CCA ATC CTG GAG CTT GAA AAT CTG CCG CAG AAT GGC CGC CAG TGT TAC AGC TGC AAG GGG   189
Gly Pro Ile Leu Glu Leu Glu Asn Leu Pro Gln Asn Gly Arg Gln Cys Tyr Ser Cys Lys Gly
 40                  45                  50                  55                  60

AAC AGC ACC CAT GGA TGC TCC TCT GAA GAG ACT TTC CTC ATT GAC TGC CGA GGC CCC ATG AAT   252
Asn Ser Thr His Gly Cys Ser Ser Glu Glu Thr Phe Leu Ile Asp Cys Arg Gly Pro MET Asn
                 65                  70                  75                  80

CAA TGT CTG GTA GCC ACC GGC ACT CAC GAA CCG AAA AAC CAA AGC TAT ATG GTA AGA GGC TGT   315
Gln Cys Leu Val Ala Thr Gly Thr His Glu Pro Lys Asn Gln Ser Tyr MET Val Arg Gly Cys
             85                  90                  95                 100

GCA ACC GCC TCA ATG TGC CAA CAT GCC CAC CTG GGT GAC GCC TTC AGC ATG AAC CAC ATT GAT   378
Ala Thr Ala Ser MET Cys Gln His Ala His Leu Gly Asp Ala Phe Ser MET Asn His Ile Asp
        105                 110                 115                 120

GTC TCC TGC TGT ACT AAA AGT GGC TGT AAC CAC CCA GAC CTG GAT GTC CAG TAC CGC AGT GGG   441
Val Ser Cys Cys Thr Lys Ser Gly Cys Asn His Pro Asp Leu Asp Val Gln Tyr Arg Ser Gly
    125                 130                 135                 140

GCT GCT CCT CAG CCT GGC CCT GCC CAT CTC AGC CTC ACC ATC ACC CTG CTA ATG ACT GCC AGA   504
Ala Ala Pro Gln Pro Gly Pro Ala His Leu Ser Leu Thr Ile Thr Leu Leu MET Thr Ala Arg
145                 150                 155                 160                 165

CTG TGG GGA GGC ACT CTC CTC TGG ACC TAA ACC TGA AAT CCC CCT CTC TGC CCT GGC TGG ATC   567
Leu Trp Gly Gly Thr Leu Leu Trp Thr
                170

CGG GGG ACC CCT TTG GAA TTC C                                                         589
```

PMN 600

FIG. 12

```
GAATTCGGGTGCAGGGACCCCGCGCACAGGAGCTGCCCTCGCGAC ATG GGT CAC CCG CCG CTG CTG CCG CTG    72
                                              MET Gly His Pro Pro Leu Leu Pro Leu
                                               1               5

CTG CTG CTG CTC CAC ACC TGC GTC CCA GCC TCT TGG GGC CTG CGG TGC ATG CAG TGT AAG ACC   135
Leu Leu Leu Leu His Thr Cys Val Pro Ala Ser Trp Gly Leu Arg Cys MET Gln Cys Lys Thr
 10                  15                  20                  25                  30

AAC GGG GAT TGC CGT GTG GAA GAG TGC GCC CTG GGA CAG GAC CTC TGC AGG ACC ACG ATC GTG   198
Asn Gly Asp Cys Arg Val Glu Glu Cys Ala Leu Gly Gln Asp Leu Cys Arg Thr Thr Ile Val
                 35                  40                  45                  50

CGC TTG TGG GAA GAA GGA GAA GAG CTG GAG CTG GTG GAG AAA AGC TGT ACC CAC TCA GAG AAG   261
Arg Leu Trp Glu Glu Gly Glu Glu Leu Glu Leu Val Glu Lys Ser Cys Thr His Ser Glu Lys
             55                  60                  65                  70

ACC AAC AGG ACC CTG AGC TAT CGG ACT GGC TTG AAG ATC ACC AGC CTT ACC GAG GTT GTG TGT   324
Thr Asn Arg Thr Leu Ser Tyr Arg Thr Gly Leu Lys Ile Thr Ser Leu Thr Glu Val Val Cys
         75                  80                  85                  90

GGG TTA GAC TTG TGC AAC CAG GGC AAC TCT GGC CGG GCT GTC ACC TAT TCC CGA AGC CGT TAC   387
Gly Leu Asp Leu Cys Asn Gln Gly Asn Ser Gly Arg Ala Val Thr Tyr Ser Arg Ser Arg Tyr
     95                 100                 105                 110

CTC GAA TGC ATT TCC TGT GGC TCA TCA GAC ATG AGC TGT GAG AGG GGC CGG CAC CAG AGC CTG   450
Leu Glu Cys Ile Ser Cys Gly Ser Ser Asp MET Ser Cys Glu Arg Gly Arg His Gln Ser Leu
115                 120                 125                 130                 135

CAG TGC CGC AGC CCT GAA GAA CAG TGC CTG GAT GTG GTG ACC CAC TGG ATC CAG GAA GGT GAA   513
Gln Cys Arg Ser Pro Glu Glu Gln Cys Leu Asp Val Val Thr His Trp Ile Gln Glu Gly Glu
                140                 145                 150                 155

GAA GGG CGT CCA AAG GAT GAC CGC CAC CTC CGT GGC TGT GGC TAC CTT CCC GGC TGC CCG GGC   576
Glu Gly Arg Pro Lys Asp Asp Arg His Leu Arg Gly Cys Gly Tyr Leu Pro Gly Cys Pro Gly
            160                 165                 170                 175

TCC AAT GGT TTC CAC AAC AAC GAC ACC TTC CAC TTC CTG AAA TGC TGC AAC ACC ACC AAA TGC   639
Ser Asn Gly Phe His Asn Asn Asp Thr Phe His Phe Leu Lys Cys Cys Asn Thr Thr Lys Cys
        180                 185                 190                 195
```

FIG. 13A

```
AAC GAG GGC CCA ATC CTG GAG CTT GAA AAT CTG CCG CAG AAT GGC CGC CAG TGT TAC AGC TGC   702
Asn Glu Gly Pro Ile Leu Glu Leu Glu Asn Leu Pro Gln Asn Gly Arg Gln Cys Tyr Ser Cys
    200                 205                 210                 215

AAG GGG AAC AGC ACC CAT GGA TGC TCC TCT GAA GAG ACT TTC CTC ATT GAC TGC CGA GGC CCC   765
Lys Gly Asn Ser Thr His Gly Cys Ser Ser Glu Glu Thr Phe Leu Ile Asp Cys Arg Gly Pro
220                 225                 230                 235                 240

ATG AAT CAA TGT CTG GTA GCC ACC GGC ACT CAC GAA CCG AAA AAC CAA AGC TAT ATG GTA AGA   828
MET Asn Gln Cys Leu Val Ala Thr Gly Thr His Glu Pro Lys Asn Gln Ser Tyr MET Val Arg
                245                 250                 255                 260

GGC TGT GCA ACC GCC TCA ATG TGC CAA CAT GCC CAC CTG GGT GAC GCC TTC AGC ATG AAC CAC   891
Gly Cys Ala Thr Ala Ser MET Cys Gln His Ala His Leu Gly Asp Ala Phe Ser MET Asn His
            265                 270                 275                 280

ATT GAT GTC TCC TGC TGT ACT AAA AGT GGC TGT AAC CAC CCA GAC CTG GAT GTC CAG TAC CGC   954
Ile Asp Val Ser Cys Cys Thr Lys Ser Gly Cys Asn His Pro Asp Leu Asp Val Gln Tyr Arg
        285                 290                 295                 300

AGT GGG GCT GCT CCT CAG CCT GGC CCT GCC CAT CTC AGC CTC ACC ATC ACC CTG CTA ATG ACT  1017
Ser Gly Ala Ala Pro Gln Pro Gly Pro Ala His Leu Ser Leu Thr Ile Thr Leu Leu MET Thr
    305                 310                 315                 320

GCC AGA CTG TGG GGA GGC ACT CTC CTC TGG ACC TAAACCTGAA ATCCCCCTCT CTGCCCTGGC         1080
Ala Arg Leu Trp Gly Gly Thr Leu Leu Trp Thr
325                 330                 335

TGGATCCGGG GGACCCCTTT GCCCTTCCCT CGGCTCCCAG CCCTACAGAC TTGCTGTGTG ACCTCAGGCC         1150

AGTGTGCCGA CCTCTCTGGG CCTCAGTTTT CCCAGACTAT GAAAACAGCT ATCTCACAAA GTTGTGTGAA         1220

GCAGAAGAGA AAAGCTGGAG GAAGGCCGTG GCAATGGGAG AGCTCTTGTT ATTATTAATA TTGTTGCCGC         1290

TGTTGTGTTG TTGTTATTAA TTAATATTCA TATTATTTAT TTTATACTTA CATAAAGATT TTGTACCAGT         1360

GGAAAAAAAA AAAAAAAAAA AAAAAAAAAA AAAAAAAAAA AGAATTC                                  1407
```

FIG. 13B

```
     THWIQEE---IGRPKDDRHLRGYLPGCPGSNGFHNDTFHFLK
2) hPIP
3) hP-PLA2   AVWQFRKMIKCVIHP--GS-DPFLEYNYCGCL--GG--SGTPVDELDK
4) C.atrox   SLVIQFETLIMK-IAGRSGLLWYSAYGCYCG--WGG--HGLPQDATDR

             CCNTKCNEGPHA-----ELENLPQNGRQCYSCKGNSTCSSEE
2) hPIP
3) hP-PLA2   CCQTHDNCYDQAK---LDSCKFLLDNPYTHTYSYSE---IC-TC
4) C.atrox   CCFVHDCCYGKA-T--DC----NPKTVSYTYS-NGEI---C--GGD

             --EAFLTDCICRGPMNQCLVATG-THEPKNQYMVR-GCATASM-C
2) hPIP
3) hP-PLA2   KECEAFICNCDRNAAICFSKAPYNKAH--TKKLD-YCQSREEPC
4) C.atrox   DPCGTQLICECDKAAAICFRDNIPSYD-NKYWLFPPKDCREEPC
```

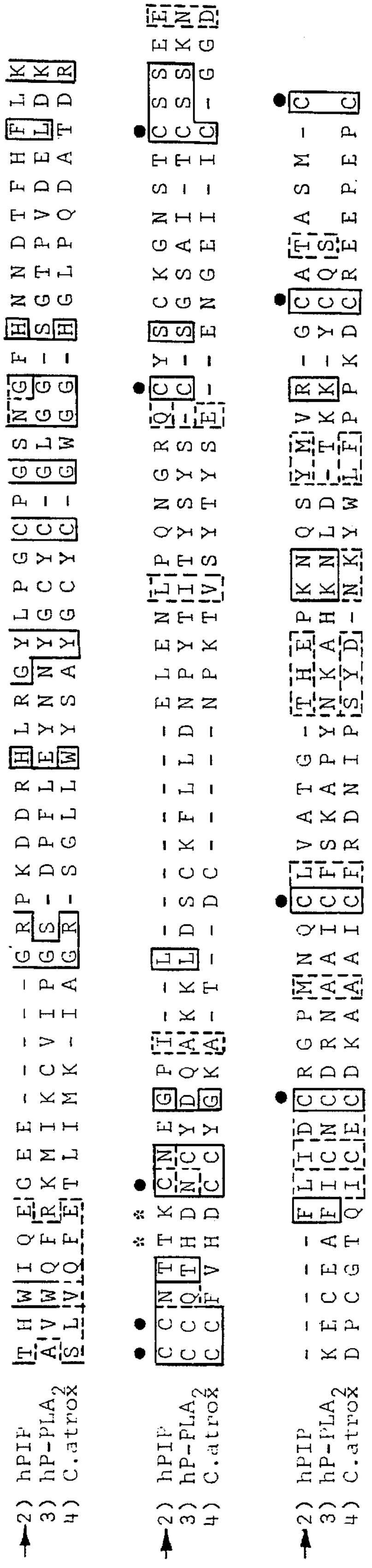

FIG. 17

ANTIBODIES FOR HUMAN PHOSPHOLIPASE INHIBITORY PROTEIN (HPIP)

CROSS-REFERENCE TO RELATED APPLICATION

This application is a division of application Ser. No. 08/115,316 filed Sep. 1, 1993, now U.S. Pat. No. 5,542,764 which is divisional of 07/871,577 filed Apr. 20, 1992, now U.S. Pat. No. 5,264,550 which is a continuation of 07/538,692 filed Jun. 14, 1990 now abandoned, which is a continuation of 06/883,598 filed Jul. 9, 1986, abandoned which is a continuation-in-part of 06/723,046 filed Apr. 15, 1985, abandoned.

TECHNICAL FIELD

The invention relates to the field of treating inflammation in humans and animals. More particularly, the invention concerns a pure preparation of a phospholipase inhibitory protein (PIP) which is effective in controlling inflammation.

BACKGROUND ART

The general physiological phenomenon of inflammation at the site of a wound or infection has been recognized for centuries. It is also well understood that while this phenomenon may be of positive value in response to such stimuli, the extent of this response must often be controlled in order properly to secure the comfort of the human or animal subject. In addition, inflammation may occur as a chronic inflammatory disorder, such as, for example, rheumatoid arthritis or systemic lupus erythomatosis. Such conditions are debilitating in themselves and can result in often life threatening, acute episodes. The inflammation associated with another such disorder, asthma, may also result in death due to constriction of the bronchia.

Within the last few decades a more detailed picture of the biochemical events associated with inflammation has been accumulated. The picture is a complex one. Part of the initiation process is mediated by peptide kinins, such as bradykinin, which are liberated by kallikrein proteases upon tissue destruction. The kinins or other peptide messengers, act on specific cell receptors at the inflammation site to activate the phospholipase enzymes A2 and/or C, to initiate the arachidonate cascade.

The "arachidonate cascade" is of singular importance in maintaining the inflammatory response. Within this complex of reactions, illustrated in FIG. 1, arachidonic acid is liberated from membrane phospholipids of a subject cell, and converted to a variety of products known collectively as eicosanoids. The eicosanoids include the leukotrienes and prostaglandins, which are released into the extracellular environment to exert their effects directly on the inflammatory site. They have relatively short half lives. However, their physiological effects are varied and dramatic, and include vasodilation (e.g., prostacylin and leukotrienes $LTC_4$ and $LTD_4$), vasoconstriction (e.g., thromboxane and $LTB_4$), and histamine release.

Most of the members of the current repertoire of anti-inflammatory pharmaceuticals are directed against some aspect of the arachidonate cascade. From this standpoint, the significant features of the cascade, as shown in FIG. 1, are that production of all products begins with the liberation of arachidonic acid from cellular phospholipids, catalyzed by the phospholipases, and the reaction pathway then branches into several reaction series: the cyclooxygenase pathways which generate the prostaglandins and the lipoxygenase pathways which generate leukotrienes.

Most of the commonly used non-steroid anti-inflammatory drugs, such as aspirin or indomethacin, inhibit cyclooxygenase, and hence only some of the pathways by which arachidonic acid is converted to end products. Other pathways of the arachidonate cascade are not affected. Steroid, or glucocorticoid, hormones, on the other hand, generally exert their affect on the production of arachidonic acid from the phospholipid membrane sources, and thus directly effect the entire cascade. Hong, S., et al, *Proc Natl Acad Sci* (USA) (1976) 73:1730–1734. However, the disadvantages of steroid therapy are well known. Side effects such as water retention, hypoglycemia. hyperlipidemia, osteoporosis, glaucoma, and increased risk of coronary and large-vessel atherosclerosis are among the undesirable responses which may accompany such treatment.

It has recently been shown that the anti-inflammatory effect of the steroids is due, at least in part, to their ability to induce the secretion of proteins which bind to and inhibit the phospholipase enzymes which are responsible for the release of arachidonic acid. Hirata, F., *J Biol Chem* (1981) 256:7730–7733. This inhibitor has been designated macrocortin (Blackwell, R. J., et al, *Nature* (1980) 287:147–149): renocortin (Russo-Marie, F., et al, *Biochim Biophys Acta* (1982) 712:177–185): or lipomodulin (Hirata, F., et al, *Proc Natl Acad Sci* (USA) (1980) 77:2533–2536). The proteins have been partially purified from rat and rabbit cells, and appear to be immunologically cross-reactive (Hirata, F., et al, *Biochem Biophys Res Comm* (1982) 109:223–230: Rothhut. B., et al, ibid (1983) 117:878–884).

Recently, a human form of the inhibitor termed lipocortin has been identified in human fibroblasts (Errasfa, M., et al, *Biochim Biophys Acta* (1985) 847:247–254. Also Wallner, B. P., et al, *Nature* (1986) 320:77–81 and Pepinsky, R. B., et al, *J Biol Chem* (1986) 261:4239–4261, have reported the isolation and sequencing of rat lipocortin, and the cloning of its human analog, which is a PA2 inhibitor in vitro.

Direct administration of the proteins which inhibit arachidonic acid formation rather than of the glucocorticoids, which stimulate the production of these proteins, would result in the advantages of steroid control of inflammation without exposing the subject to the risk of the attendant side effects. However, the human form of this protein is not available in purified form. It would, of course, be highly desirable to have pure human phospholipase inhibiting protein (PIP) in sufficient purity and amount to permit such direct treatment of unwanted inflammatory response.

DISCLOSURE OF THE INVENTION

The invention provides purified human phospholipase inhibitory protein (hPIP) and materials useful in its production by recombinant technology. A material purified to apparent homogeneity from human peritoneal dialysis fluid having a single 40 kd band on SDS-PAGE contains substantial amounts of apolipoprotein IV (apoAIV) and significant PIP activity. Immunization of rabbits with protein eluted from this 40 kd band raises antisera capable of reacting both with apoAIV and with PIP. These antibodies are thus appropriate for screening recombinant and other cells for hPIP production.

Human PIP free from other proteins normally in association with it is obtained in two ways, by direct purification from peritoneal dialysis fluid, and by production using recombinant hosts. Accordingly, in one aspect, the invention relates to human PIP in substantially pure form. In another aspect, the invention relates to a protein having human PIP activity which comprises the amino acid sequence set forth in FIG. 13. In still another aspect, the invention relates to a process for the preparation of purified hPIP from peritoneal dialysis fluid and to the product of that process. The product of the purification process is characterized by a 36 kd or 40 kd molecular weight in the nonglycosylated or glycosylated form, respectively, and by PIP activity.

Pure hPIP may also be produced using recombinant techniques. Accordingly, other aspects of the invention relate to this recombinantly produced hPIP in both nonglycosylated and glycosylated form, to expression systems which permit production of this protein in recombinant hosts, to vectors containing the expression system, to hosts transformed with the system and to a method of producing hPIP by culturing recombinant host cells.

In still other aspects, the invention relates to the antibodies produced in response to administration of the 40 kd mixture of apoAIV and PIP and of the PIP protein of the invention itself, to pharmaceutical compositions containing PIP, and to methods for ameliorating inflammation in human and veterinary subjects using such compositions or purified PIP. It appears that PIP may be stabilized by the presence of apoAIV, and compositions containing PIP in admixture with apoAIV are specifically useful as pharmaceuticals.

BRIEF DESCRIPTION OF THE DRAWINGS

FIG. 10 shows the nucleotide and deduced amino acid sequence for the insert in pU200.

FIG. 11 shows the nucleotide and deduced amino acid sequence for the insert in pU500.

FIG. 12 shows the nucleotide and deduced amino acid sequence for the insert in p600.

FIG. 13 shows the nucleotide and deduced amino acid sequence for the insert in pLE-1 having the complete coding sequence for hPIP.

FIG. 17 shows comparative amino acid sequences for hPIP and phospholipase.

MODES OF CARRYING OUT THE INVENTION

A. Nature of the PIP Protein

Figure 1:
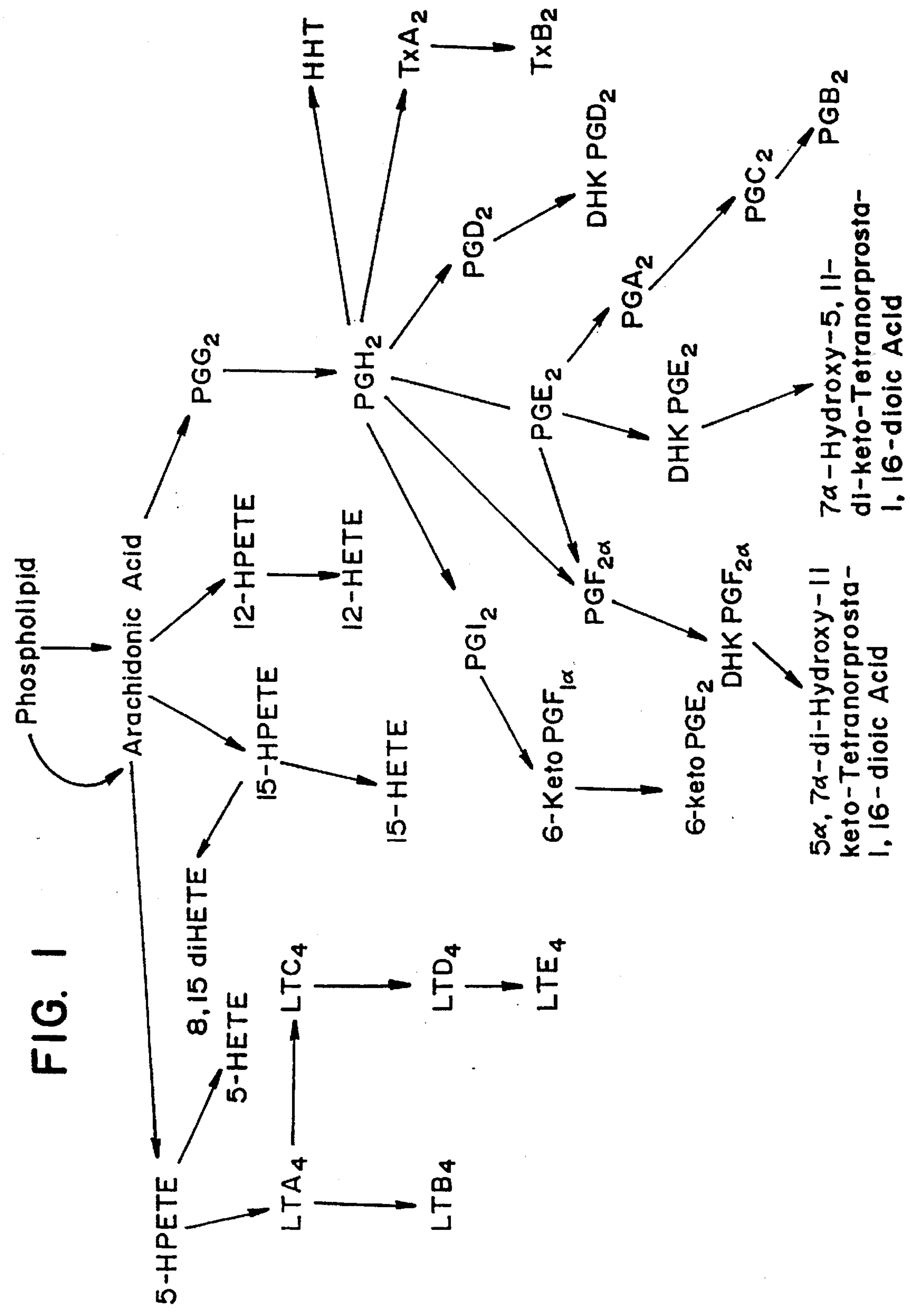
FIG. 1 shows the arachidonate cascade and the eicosanoid products of the reaction scheme.

The protein of the invention has been prepared using as a starting material, human peritoneal dialysis fluid obtained from dialysis patients. A purification procedure is presented whereby the protein has been obtained in homogeneous form, free of impurities normally associated with the protein as found in its native state. While the purification procedure is successful in obtaining this protein in sufficient purity to be used therapeutically per se, the availability of the purified material is also a significant step in the development of alternative modes of preparation. Recombinant techniques for the preparation of hPIP are described herein. Accordingly, the PIP of the invention includes not only the hPIP prepared as herein described, but proteins of substantially similar structure obtained using alternative approaches. By "substantially similar" is meant that the activity of the protein in inhibiting phospholipase A2 (PA2 inhibition assay), as described in the in vitro enzymatic assay procedure set forth hereinbelow, is retained. The amino acid sequence set forth in FIG. 13 is known to exhibit this activity.

It is well recognized that amino acid sequences may be modified in various ways and still retain their fundamental activity. First, certain portions of the peptide sequence are often not essential for activity, and only a fragment of the entire natively produced protein may be required. Therefore, portions of the amino acid sequence shown in FIG. 13 are therefore included within the definition if activity is retained. Second, addition, deletion, or alteration of a particular, or a few particular, amino acids in the sequence, may result in changes which are inconsequential with regard to functionality. Third, since proteins contain ionizable hydrogen, the ionization state of the protein as neutral or salt form, is dependent on the pH of the surrounding medium, if the protein is in solution, or on the pH of the solution from which the protein is prepared in solid form. In addition, the amino acids of the sequence may undergo minor alterations in their side chains, such as, for example, oxidation of sulfhydryl groups, which modifications may also be ineffective in destroying activity. Finally, proteins are often found in their native states in association with non-protein residues, such as, for example, phosphate, acetyl groups, or carbohydrates. The purified or recombinant PIP protein of the invention is defined functionally, but all embodiments are expected to retain extensive primary sequence homology with the hPIP exemplified in FIG. 13. The level of homology is expected to be above 40% considering both conservative changes and exact homologies in the region of interest encoded by nucleotides 490–852 of FIG. 13. Additional variation is acceptable in other regions of the protein. All of the foregoing modifications are within the definition so long as the activity as exhibited in the in vitro phospholipase A2 (PA2) inhibition assay, set forth hereinbelow, is not destroyed.

"Active PIP fragment" refers to a peptide comprising, with respect to PIP, only the sequence encoded by the above-mentioned nucleotides 490–852 of FIG. 13. If only this fragment is used, somewhat less than 40% homology in the primary structure is required when the secondary structure is sufficiently similar, as determined by application of the standard algorithms of Chou-Fasman or Kyte-Doolittle. In particular the peptide encoded by nucleotides designated 31–381 in the lipocortin disclosed by Wallner et al (supra) provides a secondary structure filling this requirement, though the primary amino acid sequence clearly has less than 40% homology in this region. Therefore, this particular fragment is also claimed, as well as those derived from the hPIP sequence disclosed herein.

"Operably linked" refers to a juxtaposition wherein the components are configured so as to perform their usual function. Thus, control sequences operably linked to coding sequences are capable of effecting the expression of the coding sequence.

"Control sequence" refers to a DNA sequence or sequences which are capable, when properly ligated to a desired coding sequence, of effecting its expression in hosts compatible with such sequences. Such control sequences include promoters in both procaryotic and eucaryotic hosts, and in procaryotic organisms also include ribosome binding site sequences, and, in eucaryotes, termination signals. Additional factors necessary or helpful in effecting expression may subsequently be identified. As used herein, "control sequences" simply refers to whatever DNA sequence may be required to effect expression in the particular host used.

"Cells" or "recombinant host cells" or "host cells" are often used interchangably as will be clear from the context. These terms include the immediate subject cell, and, of course, the progeny thereof. It is understood that not all progeny are exactly identical to the parental cell, due to chance mutations or differences in environment. However, such altered progeny are included when the above terms are used.

B. Purification of PIP From Dialysis Fluid

Figure 2:
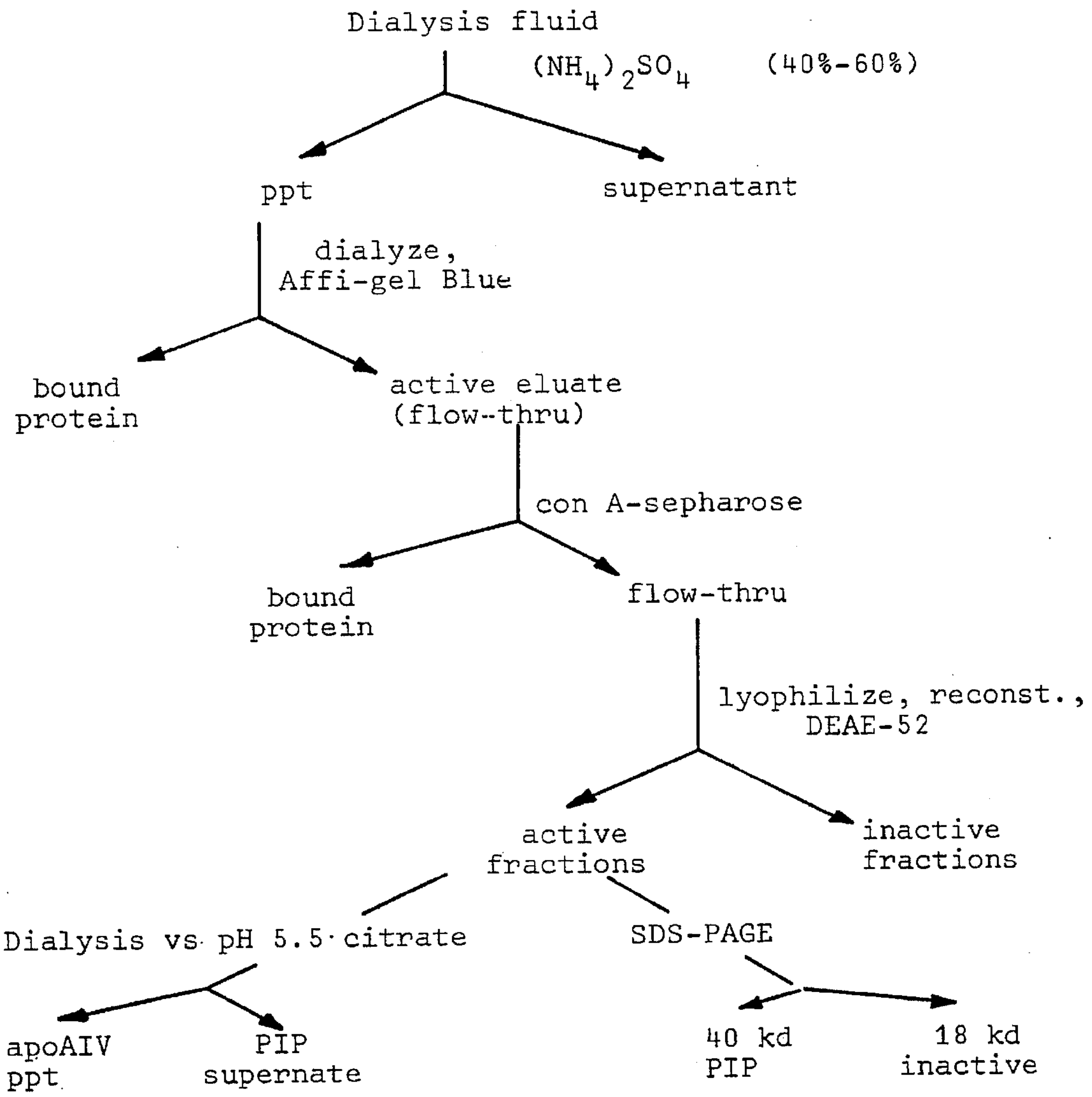
FIG. 2 shows an outline of the purification procedure used herein.

In general, the purification of the hPIP of the invention was carried out as set forth in FIG. 2. Alternative approaches are, of course, possible, but the procedure there set forth results in a homogeneous active preparation. The approach summarized with respect to the specific procedure as set forth in FIG. 2 is, briefly, as follows:

Dialysis fluid sufficient to yield approximately 2 l of fluid is conveniently obtained in one batch from patients undergoing continuous ambulatory peritoneal dialysis. Successive 2 l batches are processed as described below to obtain the desired quantity of pure product. The fluid is first subjected to increasing concentrations of ammonium sulfate: the fraction precipitated at approximately 40%–60% ammonium sulfate saturation contains the activity and is subjected to further purification. It is helpful to pre-precipitate proteins which are insoluble at less than 40% ammonium sulfate. The precipitates are recovered by centrifugation and then subjected to further purification.

In order to lower the salt concentration, the ammonium sulfate-containing fraction is dissolved in a suitable buffer of approximately pH 8 and then dialyzed against the same or comparable buffer at low temperature.

The dialyzate is then subjected to a treatment which removes the albumin component, the largest quantity contaminant. Chromatography on the affinity support Affi-gel blue previously equilibrated in the same buffer is suitable for this purpose. The desired PIP-containing fraction is not bound to the column under these conditions and appears in the flow-through volume, although contaminating proteins in the solution are retained by the column and are eluted at higher salt concentration.

The PIP fractions are treated with a lectin support, such as, for example, concanavalin-A sepharose, lentil lectin-sepharose, or peanut agglutinin-sepharose, preferably concanavalin-A sepharose eguilibrated with similar pH 8 buffer. Again the desired activity does not adhere to the column under these conditions.

The PIP-containing flow through fractions are further purified by anion-exchange chromatography, using, for example, DEAE cellulose, QAE-cellulose, or SP-cellulose, preferably DEAE cellulose, equilibrated in a similar buffer at approximately pH 8. The hPIP adsorbs to the column and fractions are eluted using a convenient salt gradient. The PA2 inhibitory activity of the eluate fractions is measured to ascertain the desired PIP fractions.

When the active fractions are subjected to preparative SDS-PAGE, SDS-PAGE yields an 18 kD band of inactive protein, and an active 40 kD band. The 40 kD band was eluted and reconstituted in the absence of detergent, to obtain protein exhibiting the desired activity. The preparative procedure is conducted substantially as described by Laemli, U. K., *Nature* (1970) 23:680–685; and an approximately 3 mm 12.5% gel is appropriate to purify a mixture containing 10 mg total protein.

The 40 kd band obtained as described has high PIP activity as demonstrated in a number of in vitro and in vivo assays as described in section D below, but contains, in addition to PIP, apoAIV and additional protein(s) of similar molecular weight. It is believed that apoAIV following PIP through this purification procedure confers stability on PIP, and that PIP may occur in situ as an apoAIV complex. Once isolated from apoAIV as described below, PIP becomes relatively labile. Therefore, it may be advisable to prepare PIP in pharmaceutical compositions in the form of this complex.

The association of PIP activity with a 40 kd protein was further confirmed by performing analytical RP-HPLC on the active fractions resulting from concanavalin-A sepharose treatment. The RP-HPLC resulted in a separation wherein the activity was present in only one of a multitude of protein-containing eluted peaks. The active peak, when subjected to SDS-PAGE, yielded a single 40 kd band.

In addition, as further described below, the 40 kd band, when injected into rabbits, yielded polyclonal antisera capable of immunoreaction so as to bind PA2 inhibitory activity and so as to bind protein capable of forming a complex with phospholipase A. Therefore, although the immunogen also contains apoAIV, the elicited antibodies are reactive with PIP.

However, it is also possible to isolate human PIP free from associated proteins by subjecting the active eluate from anion exchange chromatography described above to isoelectric precipitation using sodium citrate buffer, pH 5.5, as shown in FIG. 2. Dialyzing the active fractions against this buffer results in the precipitation of non-PIP contaminants, including apoAIV. The supernatant contains the human PIP, which is recovered as a pure 40 kd band by electrophoresis, as described above.

C. Utility and Administration

The PIP proteins of the invention show in vitro activity as phospholipase inhibitors, are capable of suppressing the production of $PGE_2$ in cell culture, and are effective in several in vivo models in combatting inflammation. Accordingly, the proteins of the invention are useful in ameliorating, treating, or reducing undesirable inflammatory symptomologies in human and veterinary subjects. The proteins of the invention are useful both to control inflammatory responses which are excessive, but formed in response to external stimuli such as infection or wounding, and to treat inflammatory disorders such as rheumatoid arthritis, asthma, unwanted edema, dermatitis, arthritis, conjunctivitis, allergies, and lupus erythomatosis.

Administration of the proteins of the invention is in a general dosage range of approximately 0.1–100 μg/kg, more preferably 0.1–10 μg/kg per host body weight. The quantity administered depends, of course, on the nature of the subject, the severity of the condition to be treated, and on the mode of administration. Intravenous injection, for example, generally requires smaller amounts than alternative routes. The PIP protein may be administered in a single dose, over several partial doses, or by constant infusion over a extended time period until the desired benefits are obtained.

The protein may be administered in aqueous solution or in the presence of additional pharmaceutical excipients, depending on the mode of administration desired. Protein pharmaceuticals are desirably administered by injection, such as subcutaneous, intravenous, or intramuscular injection, or parenterally through a membrane transfer. Aerosol or oral administration may also be possible in the presence of stabilizing compositions. Complexation with apoAIV is stabilizing to PIP in these compositions, as well as in forms intended for injection.

Injectable are prepared in conventional forms as liquid solutions or suspensions, in solid form suitable for reconstitution prior to injection, or as emulsions, either of PIP or of its apoAIV complex. Suitable excipients are, for example, water, saline, dextrose, and the like. Minor amounts of auxilliary substances such as buffering agents, emulsifying agents, and so forth Ray also be included.

Suppository administration may additionally employ binders and carriers such as polyalkylene glycols and triglycerides: aerosol administration, which would be especially suitable for relief of bronchial problems generally utilizes the PIP protein or its complex in finely divided form along with a surfactant and propellant. Typical surfactants include fatty acid esters: typical propellants are the lower alkanes or fluorinated alkanes, such as freon. Topical administration in the form of lotions or salves is also practical, and is preferred in the case of localized treatment.

Both the 40 kd SDS-PAGE eluate containing both PIP and apoAIV and the purified PIP protein of the invention are also useful in order to prepare antisera or monoclonal antibodies for immunoassays useful in diagnosis and in monitoring of therapy. Design of immunoassays is well understood in the art, and can take a variety of permutations. Either competitive antigen or antibodies can be labeled using radioactive materials, fluorescent materials, or enzymes. The assay may be conducted as a direct detection of the antigen-antibody complex, as a competition assay for immunocomplexing, or as a sandwich assay wherein the complex is further immunoreactive with an additional antibody. The assays may employ standard procedures: the contribution of the invention is the provision of suitable antigen, both for direct use as standards or competitive antigen for conduct of such assays and as antibody raising material for the preparation of suitable antisera.

D. Examples

The following describes an illustrative procedure for purification of hPIP. It is not to be construed as limiting, as additional variations may clearly be employed to result in an active, pure protein. However, the specific procedure presented does, in fact, result in a homogeneous (to SDS-PAGE) preparation of a 40 kd protein having hPIP activity, and in the preparation of human PIP free from associated proteins.

D.1. Purification of hPIP from Dialysis Fluid

Human PIP was isolated from dialysis fluid using a phospholipase (PA2) inhibition assay to monitor purification. Approximately 2 1 of human peritoneal lavage fluid, obtained from a patient by continuous ambulatory peritoneal dialysis, was clarified by filtration through cheesecloth, and subjected to ammonium sulfate fractionation. Solid ammonium sulfate sufficient to obtain 40% saturation was provided, the resulting precipitate centrifuged at 10,000×g for 20 min and the supernatant recovered. Sufficient solid ammonium sulfate was added to the supernate to provide 60% saturation, and the centrifugation process repeated. The precipitate, which contained the PA2 inhibition activity, was dissolved in 20 mM ammonium bicarbonate. pH 7.8 buffer (buffer A) containing 1 mM phenyl methyl sulfonyl fluoride (PMSF) and aprotinin at 50 μg/ml. The reconstituted solution was dialyzed against buffer A at 4° C. to lower the total salt concentration, and shown to be active in the in vitro PA2 inhibition assay set forth below.

Figure 3A:
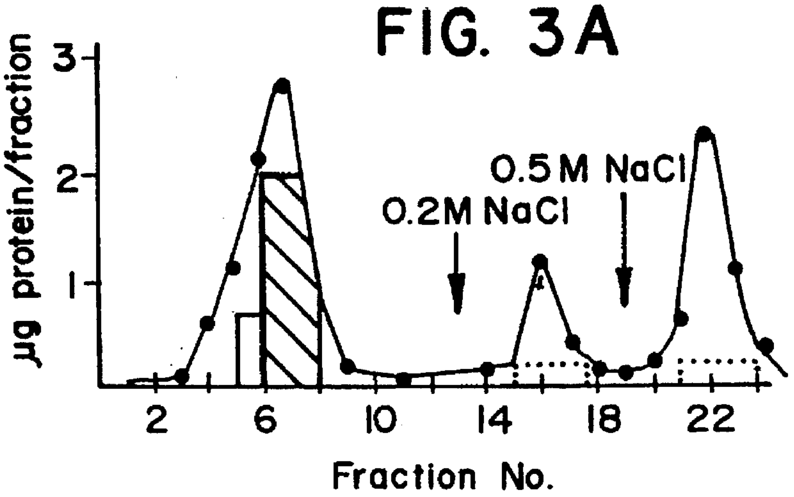
FIG. 3 shows elution patterns obtained when the 40%–60% saturation ammonium sulfate fraction of peritoneal dialyzate is subjected to Affi-gel blue, concanavalin A-sepharose, and DEAE cellulose chromatography.
Figure 3B:
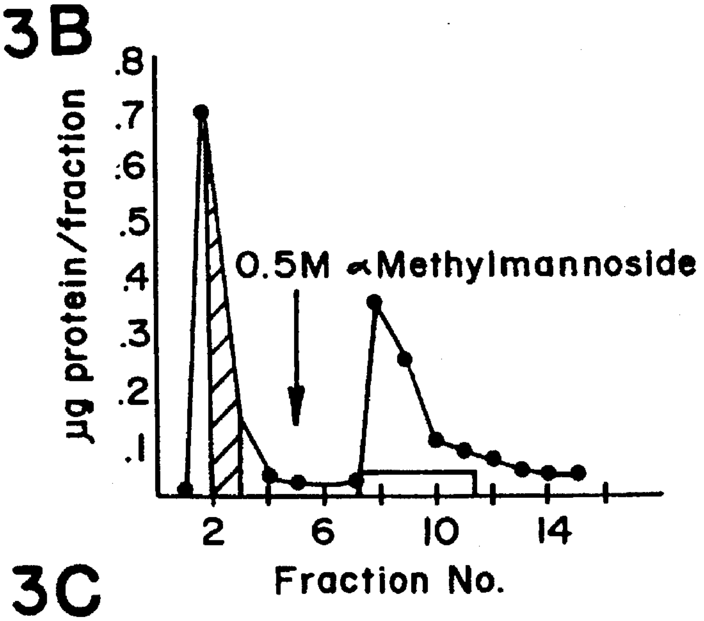

A portion of the dialyzate containing 50 mg of protein was applied to a 2.5 cm×12 cm Affi-gel blue (BioRad Laboratories, Richmond, Calif.) column pre-equilibrated in buffer A. Two ml fractions were collected at a flow rate of 0.3 ml/min. The column was eluted with a NaCl salt gradient from 0–0.5M NaCl. Fractions were assayed for PA2 inhibition activity, and all activity was shown to be in the flow through volume, as shown in FIG. 3*a*. (In FIGS. 3*a*–3*c* the solid bars indicate PIP activity.)

The active fractions were pooled, lyophilized, and then reconstituted and applied to a 2.5 cm×12 cm concanavalin-A sepharose column pre-equilibrated in buffer A. Elution at a flow rate of 0.2 ml/min yielded the elution profile shown in FIG. 3*b*. Again, all activity, as assayed by the in vitro PA2 inhibition assay, was found in the flow through volume. The active fractions were pooled and lyophilized. A small portion of the active fraction pool was set aside for RP-HPLC analysis, as described below.

Figure 3C:
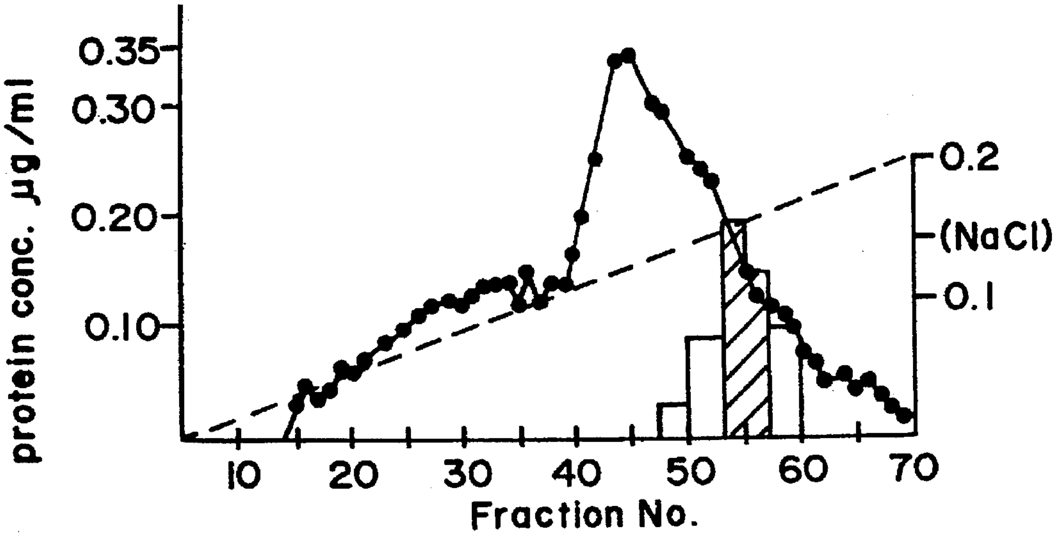

The lyophilized fractions were then reconstituted in buffer A and applied to a 2.5 cm×12 cm column of DEAE-52 pre-equilibrated in buffer A and elution conducted using a 0–0.2M linear NaCl gradient. FIG. 3*c* shows the elution profile, and the presence of activity in fractions eluted at approximately 0.125M NaCl.

The active DEAE eluate fractions were pooled, concentrated, desalted, and approximately 10 mg of the protein was loaded onto a 3 mm 12.5% polyacrylamide gel for electrophoresis separation according to the procedure of Laemli (supra) except that the disulfide bonds were not reduced with β-mercaptoethanol prior to fractionation. Protein bands were detected by a 3 staining procedure using 0.1% Coomassie blue in 50% trichloroacetic acid, followed by 5 min of destain in 5% acetic acid solution. Only two major protein bands resulted: one at 18 kD and the other at 40 kD. These bands were cut from the gel, minced into 9 $mm^3$ cubes and the protein was eluted in buffer A overnight at 4° C.

The elutate was treated to remove glycine, SDS and dye in several steps: first, the eluate was dialyzed against buffer A for 24 hr, and the dialyzate then concentrated by lyophilization. The lyophilized material was reconstituted in buffer A and extracted 3 times with 2 volumes of water saturated butanol. The aqueous layer including the interface was dried under nitrogen to remove remaining butanol and then allowed to stand at 4° C. at 1 mg protein/ml for at least 24 hr to complete protein refolding. Upon assay in the PA2 inhibition in vitro assay, the 40 kD band was active, but the 18 kD band was not.

Figure 4:
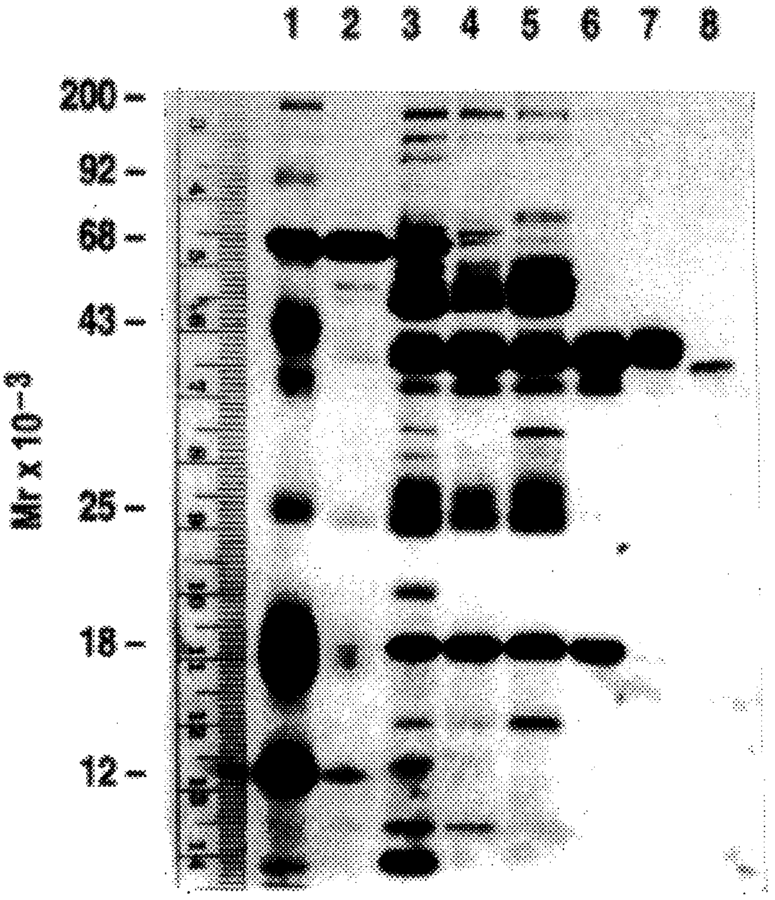
FIG. 4 shows the results of SDS-PAGE on unpurified and purified fractions of peritoneal dialysis fluid.
Figure 5:
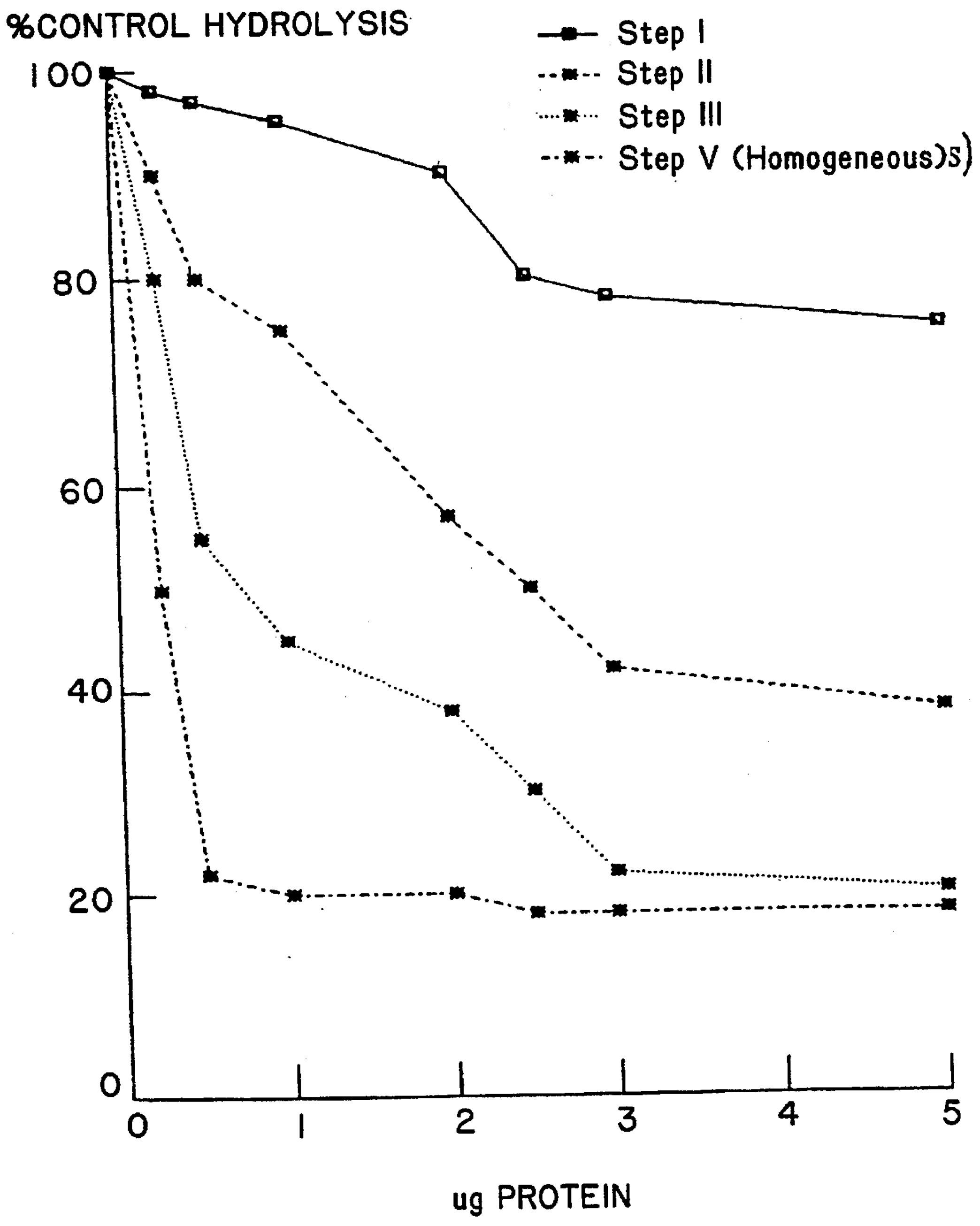
FIG. 5 shows relative PIP activity at various stages of the purification scheme.

FIG. 4 shows the comparative results of SDS-PAGE performed on the original extract, on the preparation at various stages of purification, and on the purified protein. The bands were developed using silver stain (BioRad Labs, Richmond, Calif.) by two successive oxidation and staining procedures according to the manufacturer's instructions. Lane 1 contains molecular weight markers: lane 2 is the dialysis fluid before ammonium sulfate treatment: lane 3 is the 40%×60% ammonium sulfate precipitate: lane 4 contains the pooled active fractions from Affi-gel blue chromatography: lane 5 contains pooled active fractions from concanavalin-A sepharose chromatography: lane 6 contains pooled active fractions from DEAE chromatography; lanes 7 and 8 contain 1 μg and 50 ng respectively of the 40 kD band obtained from preparative gel electrophoresis. The entire procedure results in a purification of approximately 500 fold as shown by the results illustrated in FIG. 5. Using a comparison of μg protein required for 50% inhibition, the specific activity of the crude extract is approximately 0.2% of that for the purified 40 kD band.

Figure 6:
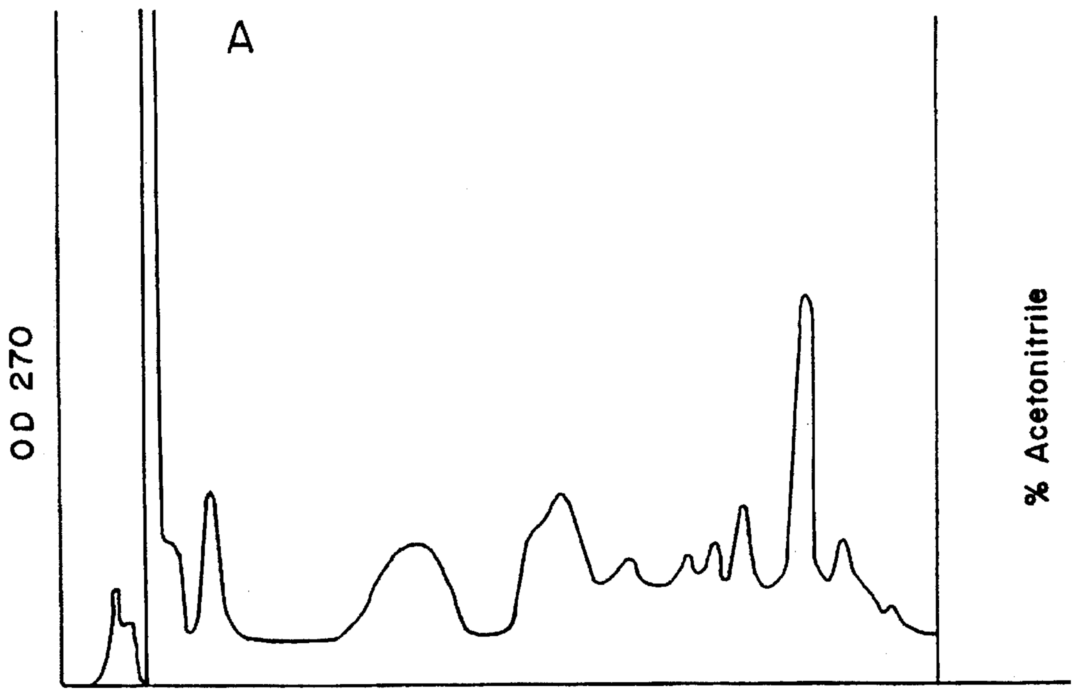
FIG. 6 shows the results of analytical reverse-phase high performance liquid chromatography (RP-HPLC) performed on the activity-containing fractions from a concanavalin A-sepharose column.

A portion of the active fractions resulting from concanavalin-A sepharose treatment described above was subjected to RP-HPLC using a $C_8$ column and elution with a gradient of acetonitrile in 0.1% trifluoroacetic acid. FIG. 6 shows the elution profile for the column. A multiplicity of protein fractions are obtained, only one contains the activity. This active fraction was then subjected to analytical SDS-PAGE using a 12.5% gel, and the developed gels were stained with Coomassie blue G-250 or with silver reagent. Only a 40 kd band was observed in each case.

To obtain pure human PIP, the pooled active eluate from the anion exchange resin above was dialyzed against pH 5.5 sodium citrate buffer. Protein which precipitated was removed by centrifugation and the proteins in the supernatant were subjected to preparative SDS-PAGE. The 40 kd band is then recovered as described above. Alternatively the supernatant can be brought to pH 7.5 and passed through a column of PLA2-Sepharose as described by Parente, L., et al, *Life Sci* (1985) 36:1225–1231. After washing the column with 150 mM NaCl the bound hPIP is eluted with either 1.0M NaCl or 0.1M acetic acid in pure form.

D.2. Preparation of Anti-PIP Antibodies

The 40 kd band above was subsequently shown to be a mixture of proteins that includes hPIP and apolipoprotein AIV (apoAIV), as will be further described below. However, this mixture was capable of raising antibodies specifically reactive with hPIP. To obtain anti-hPIP. New England white rabbits were injected subcutaneously or intramuscularly with 200 μg of the eluted 40 kd band fraction contained in complete Freunds adjuvant. The rabbits were boosted at 3-week intervals with the same vaccine. The rabbits were then bled from the ear vein 7–10 days after the boost, and the resulting serum was tested for its ability to bind the 40 kd eluate described above, using non-immune serum as control.

For the binding assay. 500 ng of purified hPIP-containing 40 kd protein was immobilized on individual wells of a polystyrene plate, and varying dilutions of antisera added to the wells. The quantity of specifically bound antibodies was quantified using $I^{125}$-labeled protein A (Amersham. Inc.). As shown in Table 1 below, a serum dilution of 1:400 shows a significant quantity of antibodies.

TABLE 1

| | cpm Bound IgG | |
|---|---|---|
| Antiserum Dilution | Immune Serum | Non-immune Serum |
| 1:10 | 12,525 | 1,213 |
| 1:50 | 11,482 | 862 |
| 1:100 | 6,745 | 943 |
| 1:200 | 3,251 | 782 |
| 1:400 | 2,852 | 846 |

These results were confirmed by competitive displacement with free, purified hPIP-containing 40 kd protein. The 1:100 serum dilution was applied to the coated polystyrene plate (1 μg 40 kd protein/well) concurrently with varying amounts of the purified 40 kd protein with the results shown in Table 2.

TABLE 2

| μg Free 40 kd Protein | cpm Bound IgG |
|---|---|
| 0 | 13,528 |
| 0.010 | 12,014 |
| 0.10 | 7,846 |
| 1.0 | 2,005 |
| 10.0 | 1,062 |

The immunoreactivity of the antisera was further used to show the progress of purification by Western blot. The samples to be tested against the antisera were diluted 1:1 with 2×SDS: sample buffer (Laemli, supra) and 10–25 μg of protein is fractionated on 1.5 mm thick SDS-polyacrylamide gels (12.5% acrylamide). The fractionated proteins were electro-transferred to nitrocellulose sheets and immunoreactive 40 kd protein was detected with anti-hPIP antibody and $^{125}$I-Protein A, using a solution containing 5% BSA, 5% ovalbumin and 5% nonfat dry milk to block nonspecific sites. Controls were run in parallel against nonimmune rabbit serum.

Figure 7:
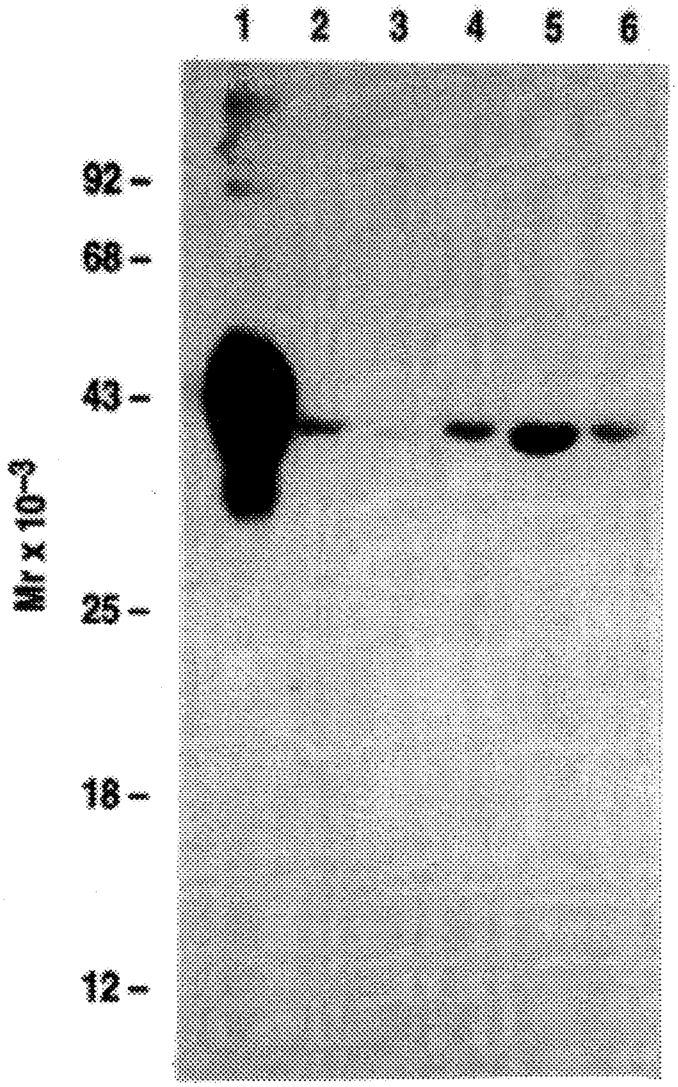
FIG. 7 displays the ability of polyclonal antisera directed against purified hPIP to detect hPIP in various fractions during the purification procedure.

FIG. 7 shows the results of Western blot performed on the same fractions shown in FIG. 4 obtained at various purification stages. Lane 1 is 43 kd $^{125}$I-ovalbumin, lane 2 is the dialysis fluid, lanes 3–5 are the active fractions from the Affi-gel Blue, Con-A sepharose and DEAE columns, respectively and lane 6 is the material obtained after preparative SDS-PAGE. The 40 kd band is specifically detected throughout purification.

Figure 8:
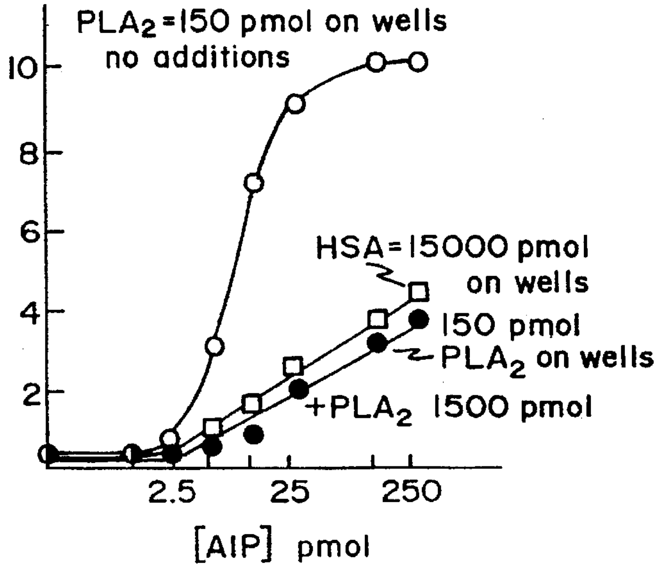
FIG. 8 shows detection of hPIP bound to PA2 by anti-40 kd antibodies.

The ability of the antisera to react specifically with hPIP, though raised in response to the 40 kd mixture, is shown by its ability to detect protein (PIP) specifically bound to phospholipase A2 (PA2), as shown in FIG. 8. PA2 (150 pmol) was immobilized on polystyrene wells and excess sites were blocked with human serum albumin. Increasing quantities of 40 kd protein were then added in the absence and presence of 1500 pmol free PA2 and binding continued for 30 min at 22° C. After washing, the bound PIP was detected using the anti-PIP antibody and $^{125}$I-protein-A. Wells containing HSA alone were also included as negative controls.

The results in FIG. 8 show that antibodies bind increasingly to the wells when increasing amounts of the PIP-containing 40 kd mixture are added; however, this binding can be reduced to the nonspecific binding level of HSA-coated wells when 1500 pmol PA2 is preincubated with the PIP-containing 40 kd mixture. Thus, the antibodies bind to a protein which itself binds to PA2, a characteristic of PIP, but not of the other components of the 40 kd mixture.

Also, preincubation of the antisera at 1:100 dilution with 10 μg of the 40 kd mixture neutralized its ability to detect protein bound to immobilized PA2.

D.3. Identification of mRNA Source for cDNA Production

The polyclonal antisera raised against the purified 40 kd protein were used to screen various human cell-sources for the production of hPIP in order to identify a source for mRNA useful to obtain a cDNA library. In a convenient screening procedure solubilized cellular protein was assayed for hPIP immunoreactivity after fractionation on SDS-polyacrylamide gels.

Candidates for screening include cultured human inflammatory cells such as the monocyte-macrophage cell lines U937 and HL60, and isolated human blood cells, such as polymorphonuclear cells (PMN), as well as lung tissue which is known to contain ~20% macrophages. The cells were incubated in appropriate culture media overnight, either containing serum or serum-free, in the presence and absence of dexamethasone (0.1 μM). Cell supernatants or the cells themselves, as appropriate, were assayed for protein immunoreactive with anti-hPIP.

For cell lysates, cells were washed free of any serum proteins and were lysed by the addition of phosphate buffered saline containing 5 mM $MgCl_2$, 0.1% NP-40, 0.1 mM PMSF, 50 μg/ml aprotinin at 4° C. Cells attached to culture plates were lysed directly on the dishes while suspension cells were collected by centrifugation and resuspended in the above buffer. After 3–5 min the lysate was collected from the culture dish and nuclei were removed by centrifugation (1000×g, 5 min).

The samples (supernatants or lysates) to be tested against the antisera were diluted 1:1 with 2×SDS: sample buffer (Laemmli, U. K., supra) and 50–100 μg of protein was fractionated on 1.5 mm thick SDS-polyacrylamide gels (12.5% acrylamide). The gels were developed as above with the addition of using anti-hPIP antisera preincubated with 50 μg of purified 40 kd protein as a control for nonspecific binding of the antibody. Following exposure of the nitrocellulose to x-ray film the hPIP immunoreactivity in several cell-types can be quantitated by densitometric scanning of the autoradiogram.

In certain cell-types hPIP is secreted into the culture media. Partially purified hPIP from such culture media are assayed as above. (In some cases, the conditioned media may be subjected to ammonium sulfate fractionation and chromatography on Affi-gel blue and Con-A sepharose. Fractions which do not bind to the Con-A sepharose column are lyophilized and analyzed for hPIP immunoreactivity on Western gels as described.)

Figure 9:
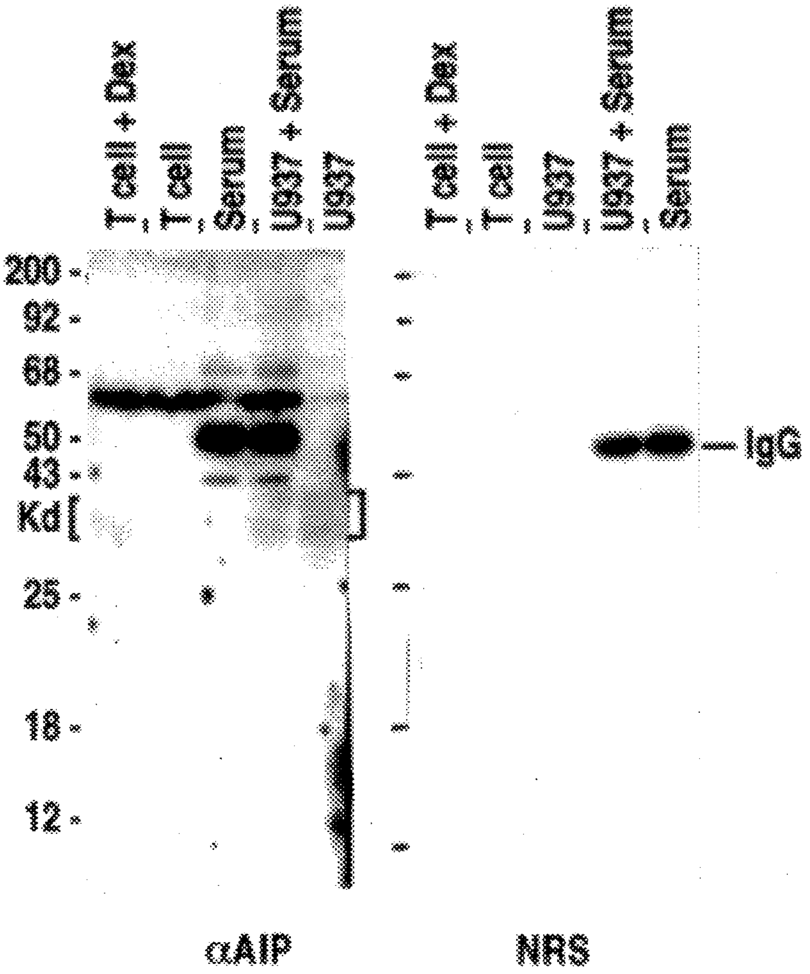
FIG. 9 shows the results of Western Blot for cells producing hPIP.

FIG. 9 shows the results obtained from both serum-containing and serum-free media conditioned for 48 hours by U937 cells.

The PIP protein appears as a 37 kd band in the medium from serum-free cultured cells. The immunoreactive band at ~40,000 daltons is most probably apoAIV, as it is present in serum and in serum-containing U937-conditioned media, but not in serum-free U937-conditioned media. Likewise, the immunoreactive band seen at ~68,000 daltons represents albumin contained in the serum. The 50,000 dalton band is the IgG heavy chain, as it is only seen in serum-containing media and is also detected when nonimmune antiserum is used; the IgG heavy chain can bind $^{125}$I-protein A independent of the antibody used to probe the Western.

These results were confirmed by assaying the same samples derived from serum-free U937-conditioned media for PA2 inhibitory activity, as shown by inhibition of $PGE_2$ production in cultured mouse fibrosarcoma cells (see below). U937 cells were therefore selected to prepare a cDNA expression library for subsequent antibody screening.

D.4. Preparation of hPIP cDNA Construction of cDNA Libraries from Selected Cells cDNA libraries were prepared initially from U937 cells, but PMN and lung cell preparations were also used.

Total cellular RNA was prepared from the selected cells by standard procedures (Chirgwin, J. M., et al, Biochemistry (1979) 18:5294–5299). Poly $A^+$ RNA was isolated by two successive passes of the RNA over an oligo-dT cellulose column.

To provide the maximum likelihood of obtaining cDNA clones encoding hPIP, two separate cDNA libraries can be constructed, one using random primers (P. L. Biochemicals) and the other using an oligo-dT primer. In both cases, the first strand synthesis uses 15 μg of poly $A^+$ RNA with the appropriate primer and is synthesized by reverse transcriptase (Avian Myeloblastosis Virus) using standard reaction conditions.

The second strand of each cDNA preparation is synthesized using RNAse H (Gubber, U., et al, Gene (1983) 25:263–269) to hydrolyze the RNA from the DNA-RNA hybrid, followed by DNA polymerase (Klenow fragment) to fill-in the resulting single stranded regions, thus creating double stranded, blunt-ended cDNAs. Internal EcoRI restriction sites are protected by methylation using EcoRI methylase (New England Biolabs) according to the manufacturer's instructions, and synthetic oligonucleotide linkers containing an EcoRI site (P. L. Biochemicals) are then ligated to the blunt-ended cDNAs using $T_4$ ligase. Polymeric linkers are reduced to monomers by subsequent digestion with EcoRI, and the fragments can be screened to a specific size class by electrophoresis through low melting point agarose (1.5% agarose) and recovered, if desired.

The resulting double stranded cDNA is ligated into the unique EcoRI site of the bacteriophage, expression vector λgt11 as described by Young, R. A. and Davis, R. W., *Science* (1983) 222:778–782. Because the EcoRI site in this vector is in the correct reading frame at amino acid position 1015 of the βgalactosidase gene, any cDNA whose reading frame and orientation are also correct with respect to the EcoRI site may be expressed as a fusion protein with β-galactosidase upon induction with isopropyl thiogalactoside (IPTG). The random frequency of this occurring is one in six. (Two orientations times three reading frames.) The proteins expressed by such induced phage plaques were also screened with polyclonal antisera directed against hPIP prepared using the 40 kd protein above.

Following ligation of the cDNAs, the recombinant DNA was packaged in vitro using a commercial packaging extract (Amersham, Inc.) and the recombinant phage were titered on the host strain *E. coli* C600Hfl as described by Young, R. A., et al (supra). About 200,000 recombinants were obtained.

The cDNA library was screened by antibodies against hPIP. Appropriate titers of about $5\times10^5$ phage were incubated with *E. coli* Y1090, plated as described, and grown for 20 hr on ten 150-mm plates to yield the desired phage density (Young, R. A., et al, supra). Since the β-gal-fused PIP protein will be in the lysate, the top agar is overlayed with nitrocellulose and plates incubated overnight at 37° C. The nitrocellulose filters are then processed for antibody detection of the recombinant fusion proteins essentially as for Western blots, except that the antibody is preabsorbed with a lysate from bacteria infected with the phage vector (λgt11) alone.

In more detail, the filters were processed by first blocking nonspecific binding with 5% nonfat dry milk dissolved in PBS, 0.1% NP-40. The filters were incubated with a 1:100 dilution of the antiserum prepared above in PBS, 0.1% NP-40, 5% BSA, 5% ovalbumin, for 2 hr and then washed in PBS, 0.1% NP-40. Bound antibody was detected using $^{125}$I-protein A ($10^5$ cpm/filter) and autoradiography of the washed filters.

Using this detection procedure positive clones were purified through successive rounds of screening until all plaques in each pool are positive. False positives were identified by performing a subsequent round of screening using duplicates at 100 plaques/2 $cm^2$ overlayed with 2 $cm^2$ nitrocellulose discs, and incubating the duplicate nitrocellulose discs with antibody which has or has not been pretreated with 10 μg of hPIP-containing 40 kd protein. Antibody binding to false positive clones should still occur with antisera pretreated with hPIP.

Phage DNA prepared from the five most intense positive clones was analyzed for size of the cDNA inserts and for sequence-relatedness.

All five cDNA inserts were approximately 200 bp. One of them, designated λU-200, was subcloned into the EcoRI site of pBR329 to give pU200, and into M13mp9 and M13mp8 for sequence analysis. FIG. 10 shows the nucleotide sequence obtained and its deduced amino acid sequence. It was possible to deduce the correct reading frame from the length of the fusion proteins produced: these proteins were approximately 70 amino acids longer than the β-gal. Therefore, following the linker the inserted sequences maintained a 200 bp open reading frame, presumably from an internal portion of the PIP protein. pU200 was therefore used to probe additional cDNA libraries.

Additional Libraries-PMN

Human white cells were prepared by sedimentation of blood through 6% dextran in 0.15M NaCl. The white cells in the supernatant were collected by centrifugation, washed in PBS and used for RNA isolation. A cDNA library in λgt10 was prepared as described above, except for using λgt10 as the cloning vector. This library was referred to as the PMN library. A λgt10 library was also prepared from the U937 cells, as above.

Each cDNA library was prepared for screening by growing approximately $10^6$ phage on *E. coli* C600Hfl, and transferring plaque lysates to nitrocellulose filters. The filters were processed for hybridization as described by Benton, W. E., et al, *Science* (1977) 196:180–182. The probes were labeled by nick translation according to Maniatis, T., et al, *Cloning Manual*, and each filter was treated with $10^7$ cpm pU200 in 1 ml of hybridization buffer at 42° C. for 16 hr. The filters were then washed twice in 2×SSC, 0.1% SDS at 22° C. for 5 min, and then washed in 0.2×SSC, 0.1% SDS at a more stringent temperature (60° C.). The hybridized filters were then dried and positive signals detected by autoradiography.

The U937 λgt10 library yielded several hybridizing cDNAs, of which the longest was about 500 bp and designated λU500. The nucleotide sequence of λU500 was determined by dideoxy sequencing and is shown in FIG. 11. Comparison of FIG. 11 with FIG. 10 shows that λU200 and λU500 share approximately 50 bp at the 5' ends of each and then diverge. This divergence was later shown to be due to intron splicing, as described below.

The λgt10 PMN library yielded four hybridizing positives having sizes of 400–600 bp: the longest cDNA was designated PMN600 and dideoxy sequenced. The sequence determined for PMN600, along with the deduced amino acid sequence, is shown in FIG. 12. PMN600 not only shares the 50 bp segment common to λU200 and λU500, but its homology with λU500 extends for another approximately 200 bp. These sequences then also diverge. This divergence was shown to be due to the presence of optional 3'terminal exons in the gene, as set forth below.

Human Lung cDNA Libraries cDNA libraries in λgt10 were prepared from human lung tissue using the procedure described above. Two such libraries were obtained, one from fetal lung tissue and the other from adult lung. Lung tissue contains approximately 20% macrophage by weight, and the production of PA2 inhibitors from guinea pig lungs has been reported. (Flower, R. J., et al, *Nature* (1979) 278:456–459.)

The fetal lung library was probed as described above using a synthetic oligonucleotide of the sequence 5'-GAAGGTAGCCACAGCCACGG-3', which represents the bases 23–42 of the sequence of PMN600 (FIG. 12). A positively hybridizing cDNA contained additional upstream sequences which could, in fact, be mapped onto an upstream exon of the genomic clone described below. This cDNA was subcloned into pBR329, designated pSR-1 and used as follows to determine the size of the PIP encoding mRNA:

When human lung poly-$A^+$ RNA was subjected to Northern blot, using pSR-1, as probe, the mature mRNA was shown to be approximately 1400 bases in length. Primer extension analysis, using a 586 bp BamHI fragment from pSR-1 as the primer, showed that an additional 500 bases were required to obtain full-length cDNA.

A Full Length hPIP cDNA

The adult human lung cDNA library was therefore screened using two probes: PMN600 cloned into pBR329 (p600), and a synthetic oligonucleotide 5'-ATGAGCTGTGAGAGGGGCCG-3', which maps to the 5' end of pSR-1. Four positively hybridizing plaques were purified and sized, and found to contain either 1360 or 1340 bp. These cDNAs were cloned into M13mp8 and M13mp9 for dideoxy sequencing, and one of them shown to contain the full-length coding sequence for hPIP. FIG. 13 shows the complete DNA sequence and the deduced amino acid sequence encoded by this clone, pLE-1 which corresponds to a primary translation product of 331 amino acids representing a protein of approximately 36.5 kd. The mature protein is believed to begin at nucleotide 112–114, encoding leucine.

An in vitro translation product of pLE-1 was obtained by subcloning the pLE-1 insert into the transcription vector BP-6 with the addition of RNA polymerase (SP6 System, Amersham Corporation, Arlington Heights, Ill.) according to the manufacturer's instructions, and then subsequently translating the mRNA produced in a reticulocyte lysate system (Bethesda Research Laboratories, Bethesda, Md.) in vitro. The translation product showed the predicted size of 36 kd. It is believed that the discrepancy between the 36 kd protein encoded and the 40 kd protein associated with peritoneal fluid is due to glycosylation. The sequence of pLE-1 has four canonical glycosylation sites (Asn-X-Ser/

Thr) beginning at bases 625, 595, 709, and 808. This was confirmed by injecting RNA transcribed as above from SP6-pLE-1 into Xenopus laevis oocytes (which can glycosylate the primary translation product) and localizing the mature 40 kd product in the membrane fraction of the oocytes.

D.5. Isolation of Genomic Clones Encoding hPIP

The complete DNA sequence encoding hPIP was also isolated from a human genomic library. The pU200 and the NcoI fragment containing bases 198–590 from p600 were used as probes: they have no common sequences. The library, in λ Charon phage, was constructed from Sau3AI-digested human DNA by the method of Maniatis, T. (supra) pp 270. For screening, $10^6$ phage are grown and plaque lifts are performed as above using triplicate nitrocellulose filters. The filters are hybridized using the above probes, and the filters are washed under stringent conditions in 0.2×SSC, 0.1% SDS, 60° C. Plaques which are positive in duplicate are picked, eluted, and repeated for second round screening. The procedure is repeated until the phage are plaque-purified.

Figure 14:
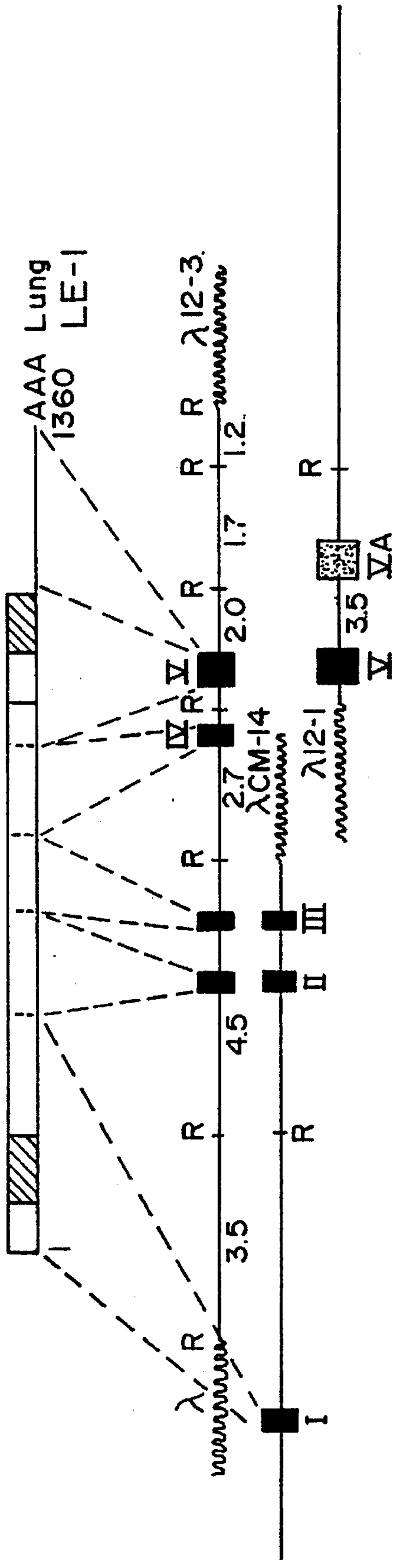
FIG. 14 shows the relationship of various cloned hPIP cDNA and genomic segments.

Two plaque-purified phage recombinants hybridizing to pU200 probe and 7 positives hybridizing to the NcoI fragment were obtained. Purified DNA from each of these clones was restricted using EcoRI and the resulting fragments blotted to nitrocellulose for probing with pU200 or the NcoI fragment. One of the recombinant phages, λ12–3, yielded fragments which were positive with both probes: λ12-3 contained exons II, III, IV and V and lacked only exon I. Additional restriction enzyme mapping showed that λ12-3 overlapped the other clones. Exon I is contained in λCM-14, a genomic clone which did not hybridize to the NcoI fragment but did hybridize to pU200. Restriction analysis and sequencing of the λ12-3 clone and further analysis of the other positive clones showed that exon V appears to be provided in an alternate form VA, as shown in FIG. 14. Exon VA, is not present in λ12-3, but is found in λ12-1, a genomic clone which hybridizes to the NcoI fragment and pU500.

Comparison of the sequences in the gene and in the cDNA clones obtained shows that the divergence of pU200 from the other clones after 50 bp is due to failure to splice out an intron, and that the divergence between PMN600 and λU500 downstream of their 250 bp homologies is due to the alternative V and VA exon availabilities. λU500 contains exon VA: PMN600 contains exon V, as does pLE-1.

D.5. Construction of Expression Vectors and Expression of hPIP

Mammalian Vectors

The cDNA clone encoding hPIP is conveniently used to produce the recombinant protein in a variety of hosts, as set forth in ¶E.1 below. However, expression in mammalian systems is favored as the host is capable of post translational processing analogous to that experienced by the natively produced protein. Either cDNA or genomic sequences may be used, as the host is also capable of processing introns.

The full length cDNA hPIP encoding clone, pLE-1 is inserted as an EcoRI fragment into the mammalian expression vector pHS1 as described below.

Construction of pHS1, the Host Expression Vector

The plasmid pHS1 contains 840 bp of the hMT-II sequence from p84H (Karin, M., et al, *Nature* (1982) 299:297–802) which spans from the HindIII site at position −765 of the hMT-II gene to the BamHI cleavage site at base +70. Plasmid p84H was digested to completion with BamHI, treated with exonuclease Bal-31 to remove terminal nucleotides, and then digested with HindIII. The desired 840 bp fragment was ligated into pUC8 (Vieira, J., et al, *Gene* (1982) 19: 259–268) which had been opened with HindIII and HincII digestion. The ligation mixture was transformed into *E. coli* HB101 to $Amp^R$, and one candidate plasmid, designated pHS1, was isolated and sequenced by dideoxy sequencing. pHS1 contains the hMT-II control sequences upstream of a polylinker containing convenient restriction sites.

Construction of hPIP Expression Vectors

The EcoRI hPIP encoding fragment, prepared as above, was ligated into EcoRI-digested pHS1 and the ligation mixture transformed into *E. coli* MC1061 to $Amp^R$. Successful transformants were screened by restriction analysis, and a strain containing the desired plasmid, pMT-PIP is further propagated to prepare quantities of plasmid DNA.

Additional expression vectors containing modified coding sequences for the hPIP protein were also prepared from modified coding sequences designated pLE-2 and pLE-3. pLE-2 lacks the sequence at the C-terminal region of the hPIP protein, which is believed to be responsible for its binding to the cellular membrane. pLE-2 was constructed by subjecting M13 phage harboring the pLE-1 sequence shown in FIG. 13 to site-directed mutagenesis to place a TAA stop codon at base 951 to replace TAC (encoding a tyrosine residue). The oligonucleotide 5'-CACTGCGTTACTGGA-3'was used as a primer and the mutated sequences were retrieved by screening the recombinant phage plaques using kinased oligonucleotide 5'-GCAGCCCCACTGCGTTACTGGACATCCAG-3'as a probe, under stringent washing of 55° C., 3M tetramethyl ammonium chloride.

The mutagenesis was confirmed by dideoxy sequencing and the single-stranded form converted to double-stranded DNA. Correct functioning of the stop codon was also confirmed by subcloning the EcoRI insert into the SP6 vector system, transcription with RNA polymerase, followed by translation in the reticulocyte lysate system. SDS-PAGE of the isolation product shows a 34 kd protein, as compared to the 36.4 kd protein obtained from full-length hPIP-encoding sequences. The SP6 mRNA was also injected into Xenopus oocytes. Media conditioned by the injected cells for 18 hr showed PIP activity as assayed by the release of labeled arachidonate from zymosan-stimulated mouse peritoneal macrophages. Media conditioned by oocytes injected with mRNA from the LE-1 sequences cloned into SP6 failed to show activity in this assay. The EcoRI insert was transferred into pHS-1, as described above for the construction of pLE-1 to give pMT-PIP(−). The ligation mixture was transformed into *E. coli* HB110 to $Amp^R$ and the correct orientation and placement confirmed by restriction analysis.

pLE-3 contains an alternate 3'-terminal sequence encoded by the VA exon which had been retrieved in pU500 above. pLE-3 was constructed by replacing the downstream sequences in pLE-1 with the appropriate fragment from pU500: pLE-1 was digested with NcoI and EcoRI and the unique 718 bp fragment purified. pU500 was digested with EcoRI and NcoI and the unique 419 bp downstream portion of the cDNA insert purified. Ligation of these fragments resulted in a 1137 bp fragment which was inserted into the EcoRI site of pUC8 and transfected into *E. coli* HB110 cells for amplification and plasmid purification. Plasmids containing the correct orientation and placement of the insert were designated pLE-3.

pLE-3 coding sequences were modified by addition of a polyadenylation signal to the 3' untranslated sequence by digesting pLE-3 with AvrII, blunting, and further digesting with EcoRI to obtain the hPIP encoding fragment. The unique 1037 bp cDNA insert was then isolated. A poly-A addition site derived from apoAI cDNA was isolated by digesting plasmid pBL13A1 (Seilhamer, J., et al, *DNA* (1984) 3:309–317) with NarI, blunting, further digesting with EcoRI, and purifying the unique 65 bp fragment containing the entire apoAI 3'untranslated region. This 65 bp fragment was ligated to the hPIP cDNA, mixed with EcoRI-digested pHSI and further ligated to yield pMT-PIP/A. The ligation mixture was then transformed into *E. coli* MC1061 to $Amp^R$. Plasmids from Amp resistant colonies were screened for the correct size insert.

For efficient secretion of the expressed hPIP it may be advantageous to employ an alternative signal sequence, such as that derived from human growth hormone, human aplolipoprotein AI, human lung surfactant, or human renin. This can be accomplished using standard procedures i.e., by digesting pLE-1. pLE-2 or pLE-3 with SphI to remove the 5' end of the cDNA, replacing lost codons of the mature protein, and ligating the appropriate signal sequences upstream therefrom. Because the first amino acid of mature hPIP is predicted to be the leucine beginning at base 112 of FIG. 13 and SphI cuts at base 124 it is necessary to reconstruct the first four amino acids using oligonucleotides encoding Leu-Arg-Cys-Met.

Production of hPIP by Mammalian Recombinants

Chinese hamster ovary (CHO)-K1 cells were grown on medium composed of a 1:1 mixture of F12 medium and DME medium with 12% fetal calf serum. The competent cells are co-transformed with pMT-PIP, pMT-PIP(−), pMT-PIP/A or pAc-PIP/A and pSV2: NEO (Southern, P., et al, *J Mol Appl Genet* (1982) 1: 327–341). pSV2: NEO contains a functional gene conferring resistance to the neomycin analog G418. In the transformation, 500 ng of pSV2-NEO and 5 μg of pMT-hPIP are applied to a 16 mm dish of cells in a calcium phosphate-DNA co-precipitate according to the protocol of Wigler, M., et al, *Cell* (1979) 16: 777–785, with the inclusion of a two minute "shock" with 15% glycerol after four hours of exposure to the DNA. A day later, the cells are subjected to 1 mg/ml G418 to provide a pool of G418-resistant colonies.

Successful transformants, also having a stable inheritance of PIP-encoding plasmid were plated at low density for purification of clonal isolates. For transformants containing PIP sequences under control of the MT promoter, small amounts of these isolates were grown in multi-well plates and induced with $10^{-4}$M zinc chloride for convenient assay. hPIP production was assayed by demonstration of inhibition of induced PA2 activity in the cultured cells.

Seventy-two hr after transfection with either pSV2:NEO or pSV2:NEO/pMT-PIP1, the cells were labeled with C-14 arachidonic acid for 2 hr. The cells were washed, stimulated with either 10% fetal calf serum or 10 μM $A_{23187}$, a calcium ionophore, both standard activators of cellular PA2, and the release of labeled arachidonic acid from the cellular membranes was measured. Cells transformed with the pSV2:NEO alone showed 30–90% more release of arachidonic acid after 20 min than those co-transfected with the pMT-PIP (see FIG. 14). Clonal isolates which produce large amounts of the desired hPIP as shown by PA2 inhibition are picked for direct assay.

For direct assay of PIP production, these cells were seeded at 1/10 confluency in basal medium supplemented with 10% fetal calf serum and grown to confluence in 850 $cm^2$ roller bottles. The cells were then washed and induced for hPIP production over 24 hr by addition of zinc chloride $10^{-4}$M and dexamethasone $10^{-6}$ in serum-free medium.

Both media and cell membrane were assayed for PIP activity. The media were harvested and concentrated by Amicon UM-100 ultrafiltration. To obtain the membrane, the cells were treated with 1 mM EDTA and collected by centrifugation at 100×g for 5 min. The cell pellet was resuspended in 2 ml of 10 mM Tris, pH 8, 250 mM sucrose, 150 mM NaCl, 1 mM EDTA, 1 mM PMSF, and broken in a glass homogenizer, monitoring the cell rupture by phase contrast microscopy. The nuclei were removed by centrifugation for 5 min at 1000×g, and the supernatant lysate was fractionated into soluble and membrane fractions by centrifugation at 100,000×g for 1 hr. The nuclear fraction was extracted with 0.1% Tween-20, and insoluble material removed by centrifugation. The membrane pellet from the lysate supernate was resuspended in homogenizing buffer, which further included 10% glycerol.

Figures 15A, 15B:
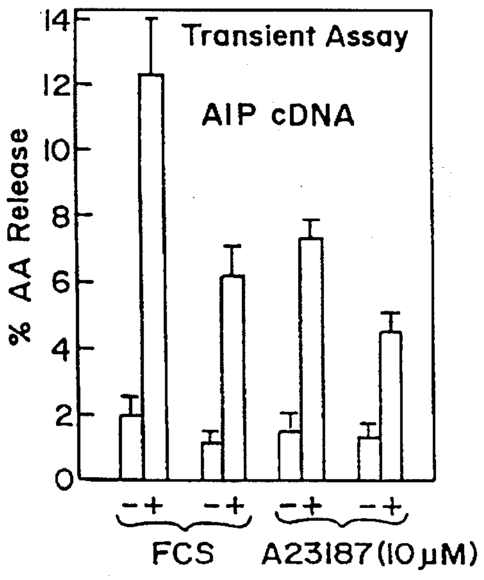
FIG. 15 shows suppression of PA2 activity in hPIP-transformed CHO cells.
Figures 16A, 16B, 16C:
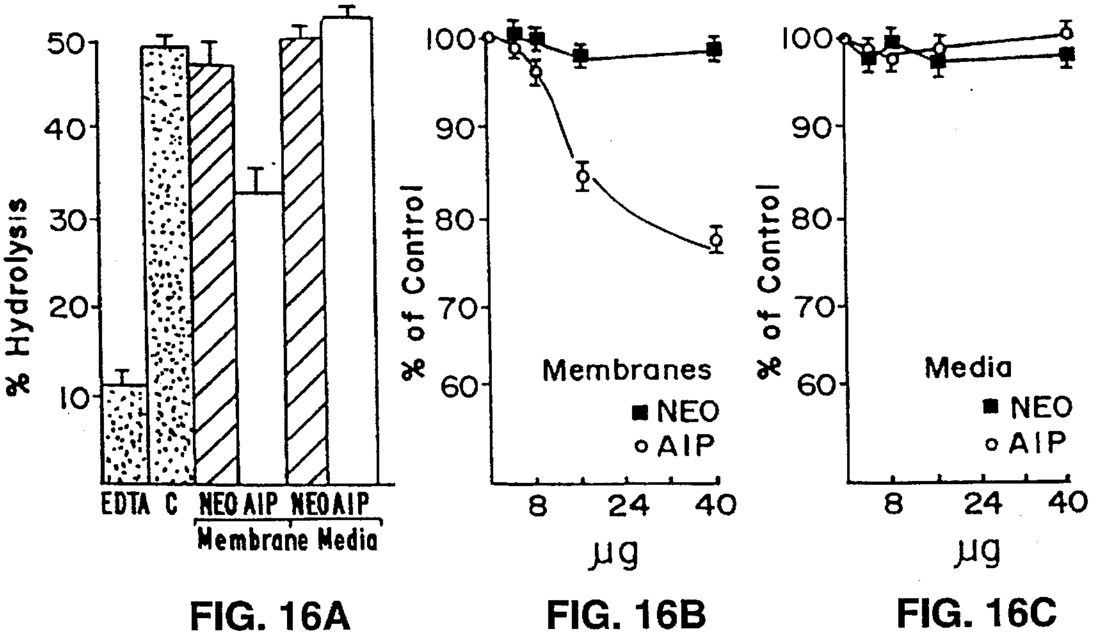
FIG. 16 shows PA2 inhibition by recombinant hPIP.

The media, cell lysate soluble fraction, membrane, and nuclear extract fractions were then assayed for PIP activity using two separate assays: Inhibition of the release of labeled arachidonic acid from the cellular membranes of zymosan-stimulated mouse resident peritoneal macrophages as described by Bonney, R. J., et al, *Biochem J* (1979) 176:433–440; and inhibition of release of C-14-labeled oleic acid incorporated into *E. coli* membranes in an in vitro assay using porcine pancreatic PA-2, as described by Vadas, P., et al, *Life Sci* (1985) 36:579–583. Only the membrane fraction shows activity in both of these assays. The other fractions obtained showed no activity. These results are shown in FIG. 15. In the *E. coli* assay, membrane from pMT-PIP-transformed cells reduced hydrolysis of *E. coli* membranes from approximately the 50% shown by the controls to approximately 30%. In the zymosan-mediated macrophage assay release was only 80% of control.

Similar results in these assays were obtained from pMT-PIP(−) transformed CHO cells, except that activity was found in the media rather than in the membrane-bound fractions.

If desired, the hPIP secreted into the medium can be purified according to the procedures set forth above for the native protein, or by other standard methods known in the art.

Bacterial Vectors and Expression

Construction of pTRP-233 Bacterial Expression Plasmid

The ten oligodeoxynucleotides shown below:

```
 1                    3                          5
5' AGAATTCAAATATTCTGAAATGAGTTGTTGACAATTAATCATCGAACTAGTTAACTAG
3' TCTTAAGTTTATAAGACTTTACTCAACAACTGTTAATTAGTAGCTTGATCAATTGATC
          2                          4                   6

             7                       9
   TACGCAAGTTCACGTAAAAAGGGTATCACATATGGTACCTGCAGA 3'
```

-continued

ATGCGTTCAAGTGCATTTTTCCCATAGTGTATACCATGGACGTCT 5'

8 10 were used to construct a synthetic trp promoter/operator. Five hundred pmole of each oligodeoxynucleotide except 1 and 10 were individually kinased using $^{32}$P-γATP. Pairs of these oligos, e.g. 1+2, 3+4, 5+6, etc, were annealed by incubating of 16.7 pmoles each at 90° C. for 2 min followed by slow cooling to room temperature, and were recovered following phenol/chloroform extraction and ethanol precipitation. The sets of pairs were ligated together with T4 ligase and the ligated DNA recovered and digested with EcoRI and PstI. The resulting DNA fragments were visualized by wet gel autoradiography and a 100 bp fragment was eluted and dideoxy sequenced to confirm the designed double stranded sequence above which contains promoter and operator regions of the trp operon and the ribosome binding site of the trp leader peptide.

Plasmid pKK233-2 (Amann, E., et al, *Gene* (1985) 40:183–190) was digested to completion with NdeI blunted, and religated to obtain the corresponding plasmid lacking the NdeI site, pKK-233-2-Nde.

Ten ng pKK-233-2-Nde was digested to completion with EcoRI and PstI, treated with CIP, and mixed with 50 ng of the synthetic EcoRI/PstI trp promoter/operator sequence described above. The mixture was ligated with T4 DNA-ligase, followed by transformation into *E. coli* JA221 lpp/ΓlacI$^q$ Transformants were screened for the presence of plasmid DNA containing the desired insert: designated pTRP-233.

Bacterial Expression Vectors for PIP

The hPIP encoding segments lacking the native signal sequence were removed from pLE-1, pLE-2, and pLE-3 by digestion with SphI, which cuts at nucleotide 114, as shown in FIG. 13, blunting with Klenow, and then digestion with HindIII which cuts at a vector site just 3' of the insert. The SphI(blunt)/HindIII fragments were ligated into the KpnI (blunt)/HindIII digested pTRP233, placing the coding sequences under control of the trp promoter, to give pTRP-PIP, pTRP-PIP(−), and pTRP-PIP/A, respectively. The ligation mixtures were transformed into *E coli* HB101 to verify correct orientation, and these transformants were grown under standard M9 salts plus 0.5% casamino acids (Difco) to OD-550 of 0.1 before induction with 25 μg/ml IAA with further growth to OD 1.0. The bacteria were then harvested, lysed with a French press or by sonication and the lysate assayed for PA2 inhibition using the in vitro assay of Vadas et al (supra).

The hPIP protein is obtained in nonglycosylated form and can be purified using standard procedures, following the purification by the PA2 inhibition assay. A fraction precipitating at 40–60% saturated ammonium sulfate is resolubilized in 25 mM Tris-HCl, pH 8.0, 2 mM EDTA, and subjected to DEAE Sephadex equilibrated with the same buffer. The protein is eluted in a NaCl gradient at 0.125M. and purified to homgeneity on a C8 HPLC column or other hydrophopbic column, from which active fractions elute at about 50% acetonitrile on a 20–100% acetonitrile gradient in 1% TFA. The dried protein in the active fractions is resolubilized in 20 mM Tris, pH 8.0, and reoxidized, if necessary, to the disulfide according to the method of Van Scherrenberg. G.M., et al, Hoppe-Seyler's Z *Physiol Chem* (1980) 361:571–576.

D.6. Active Fragments of hPIP

FIG. 17 shows a comparison of the amino acid sequences of the hPIP of FIG. 13 between nucleotide positions 490–852 with the known sequences of pancreatic and C. atrox venom phospholipases. This region of homology is suggested as sufficient for activity, by analogy with the Vipera system, which also shows homology between enzyme and inhibitor (Mancheva, I., et al, Hoppe-Seyler's Z *Physiol Chem* (1984) 345:885–894). This region of hPIP with various downstream sequences is obtained as a BstEII (blunt)/HindIII fragment from pLE-1, pLE-2, and pLE-3. (BstEII cuts at base 465.) The fragment is ligated into KpnI(blunt)/HindIII digested pTRP233, as above, to obtain pTRP-PIP(F), pTRP-PIP(F−), and pTRP-PIP(F/A) respectively. These plasmids were expressed in *E coli* as above described.

In addition, any of the above vectors can be modified to encode only the desired fragment representing the desired homologous region. This is accomplished by converting the CAA glutamine codon at nucleotide positions 853–855 to a TAA stop codon by site specific mutagenesis.

pTRP-PIP(F) is digested with HindIII and EcoRI and cloned into HindIII/EcoRI digested M13mp18. The single stranded DNA is treated with DNA polymerase using 5'-GCATGTTAGCACATT-3' as primer, and the resulting double stranded DNA transfected into competent cells. The mutagenized phage are probed with 5'-AGGTGGGCATGTTAGCACATTGAGG-3' under stringent conditions, and the purified plaques sequenced to confirm correct construction. The recovered DNA is reconstituted into double stranded form, digested with EcoRI and HindIII, and ligated into EcoRI/HindIII linearized pTRP-PIP(F). The resulting vector, designated pTRP-PIP (465–852) is transformed into *E coli* for expression. The active PIP fragment produced is then purified and reduced/oxidized as described above.

D.7. ApoAIV Sequences and hPIP Sequences

The protein obtained in ¶D.1 as a 40 kd band on SDS-PAGE contained hPIP in N-terminal blocked form and apoAIV with an N-terminus available for sequencing. When the entire fraction was subjected to sequencing using Applied Biosystems 470A gas phase sequencer, the presence of the apoAIV N-terminus was confirmed.

Approximately 50 μg of the protein were subjected to N-terminal sequencing, and PTH amino acids were identified with a Beckman 334T HPLC using an IBM CN column as described by Hunkapiller, M. W. and Hood, L. E., *Meth Enzym* (1983) 91:486–492. The N-terminal sequence obtained was Glu-Val-Ser-Ala-Asp-Gln-Val-Ala-Thr-Val-Met-Trp-Asp-Tyr-Phe-Ser-Gln-Leu-Ser-Asn-Asn-Ala-Lys-Glu-Ala-V al-Gln-Leu-Lys-Ser-Arg.

A minor secondary sequence of the 40 kd mixture could also be read. The sequence obtained was:

Glu-Asn-Leu-Pro-Gln-Asn-Gly.

Presumably the sequence arises from an internal proteolytic clip of the blocked hPIP molecule, which contains extensive disulfide bonding. This sequence begins at base 662 of the sequence shown in FIG. 13 and ends at base 693.

D.8. Activity Content of the 40 kd Band

Assay for Phospholipase A2 Inhibition

The standard in vitro inhibition assay (PA2 inhibition assay) was performed as follows:

100 ng of porcine pancreatic phospholipase AII (Sigma Chemical Co, St. Louis, Mo.) and various concentrations of the protein to be tested (up to 10 μg) were placed in 50 μl of buffer containing 20 mM Tris, pH 8.0 and 2 mM calcium ion. The solutions were incubated at 30° C. for 10 min, and then 100 μl of a solution containing 20 μg human serum albumin and 2 μCi of α-β-[I$^{14}$-C]-arachidonyl phosphatidylcholine stearoyl ($^3$H) (Amersham, Inc.) in the foregoing buffer (which solution had been sonicated 2 min in a sonication water bath at 22° C. immediately prior to addition) was added. After 15 min at 30° C., the reaction was stopped by adding 25 μl of 10 N acetic acid.

Portions 25–50 μl of the reaction mixture were applied to silica G type TLC plates for analysis in an ascending solvent system containing chloroform, methanol, acetic acid (90:10:1). Arachidonic acid was used as a standard to locate the arachidonic acid band: the phosphatidyl choline band remains at the origin. The spots were visualized by staining with iodine vapor, and the labeled arachidonate and phosphatidyl choline spots were scraped from the plate and radioactivity determined using scintillation counting in toluene-omnifluor (New England Nuclear). The percent hydrolysis was computed as a fraction 100×cpm arachidonic/(cpm arachidonic+cpm phosphatidyl choline).

Assay by $PGE_2$ Production Inhibition

The hPIP was also shown to be capable of inhibiting the production of $PGE_2$ by cultured fibrosarcoma cells. In this assay, confluent cultures of mouse fibrosarcoma cells obtained from ATCC (ATCC #CCL148) were preincubated with various concentrations of the protein to be assayed and 25 μl phosphate buffered saline in 150 μl HAMMs F10 medium (Gibco) for 15 min at 37°. One hundred μl of F10 medium containing 2% fetal calf serum was added, and the cells were incubated for an additional hour at 37° in a humidified incubator with a 5% $CO_2$/95% air atmosphere. Controls used dexamethasone (DEX) added to the cells 16 hr prior to induction. The media were removed and assayed for $PGE_2$ using a commercial radioimmunoassay kit (Seragen, Inc., Boston, Mass.).

Figure 18:
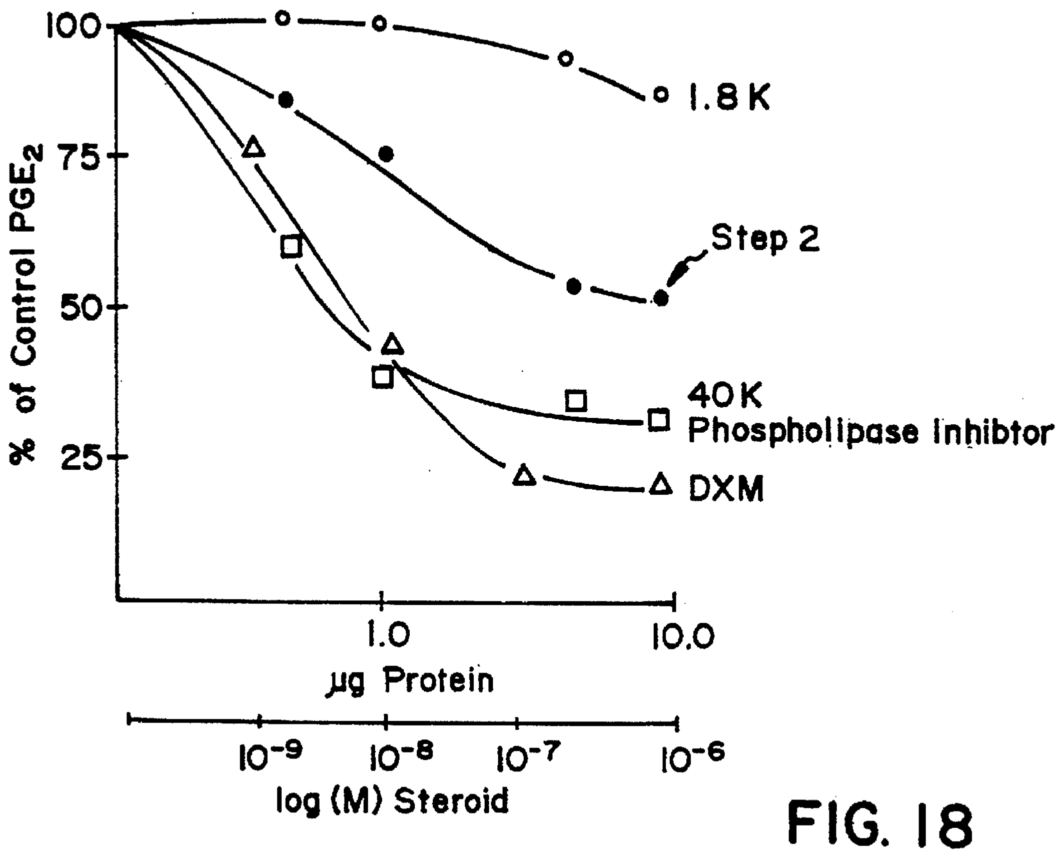
FIG. 18 shows the activity of the 40 kd protein in an in vitro assay measuring $PGE_2$ release.

FIG. 18 shows the inhibition of $PGE_2$ production by purified (by SDS-PAGE) PIP and by DEX. The 18 kD band from the gel (open circles) was used as a control. The closed circles are the results using active fractions from the Con-A Sepharose column. The squares are the results with protein from the 40 kD band: the triangles are results using DEX. The response is dose-dependent for the active proteins and for DEX. The addition of 100 μg of arachidonic acid to the cells (added at the same time PIP was applied) was able to override inhibition by both PIP and DEX.

In Vivo Assays

Three in vivo models were employed to demonstrate the activity of PIP: the rat pleurisy model, the rat paw edema model, and the adjuvant-induced arthritis model.

Figure 19:
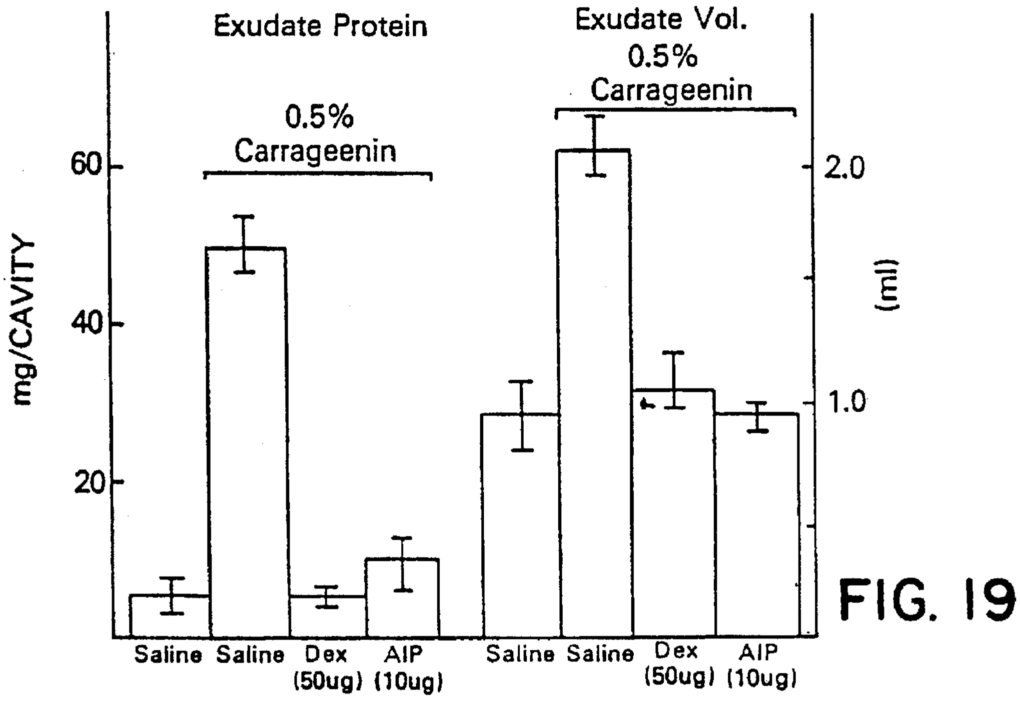
FIG. 19 shows the results of an in vivo rat pleurisy inhibition assay for hPIP activity.

In the rat pleurisy model, the pleural cavities of three groups of rats were inflamed by the injection of 0.1 ml of 0.5% carrageenin in saline, and the ability of the test substances to control the inflammation was. measured. For detection of the activity of the PIP protein, 10 μg of PIP were injected along with the carrageenin. Carrageenin injections containing 200 μg of DEX were used as positive controls. Five hours later the pleural cavity was opened, washed with 1 ml saline, the fluid volume recorded: and the protein concentration in the fluid was determined by the method of Bradford, et al, *Anal Biochem* (1976) 72:248–254. Inhibitory activity was shown by decrease in the exudate volume and exudate protein. Ten μg of the purified PIP was as effective as 200 μg DEX in suppressing both of these parameters, as shown in FIG. 19.

The data on the left record the quantity of protein exuded in mg/cavity. The quantity is reduced essentially to normal levels in the presence either of 50 μg DEX or 10 μg PIP. The measure of exudate volume is shown on the right in ml. Again either 50 μg DEX or 10 μg PIP reduce the exuded fluid volume to normal levels.

In the rat hind paw edema model, groups of male Sprague-Dawley rats (180–200 g) were lightly anesthetized under ether and hind limb edema was induced by injection of 0.1 ml of a 0.5% weight/volume carrageenin suspension into the plantar tissue of the right hind paw (Van Arnien, C., et al, *J Pharm Exp Therap* (1965) 150:328–334.

The anti-inflammatory activity of test substances was examined by administering the test substance in one of three ways: either intravenous injection, intraperitoneal injection, or co-injection with the carrageenin. Except when specified, dexamethasone administered intraperitoneally 3 hr previously, was used as a control. Results were evaluated by measuring the thickness of the hind paw with a constant-pressure caliper starting at time zero (the time of injection of the test substance), and every 60 minutes thereafter.

Figure 20:
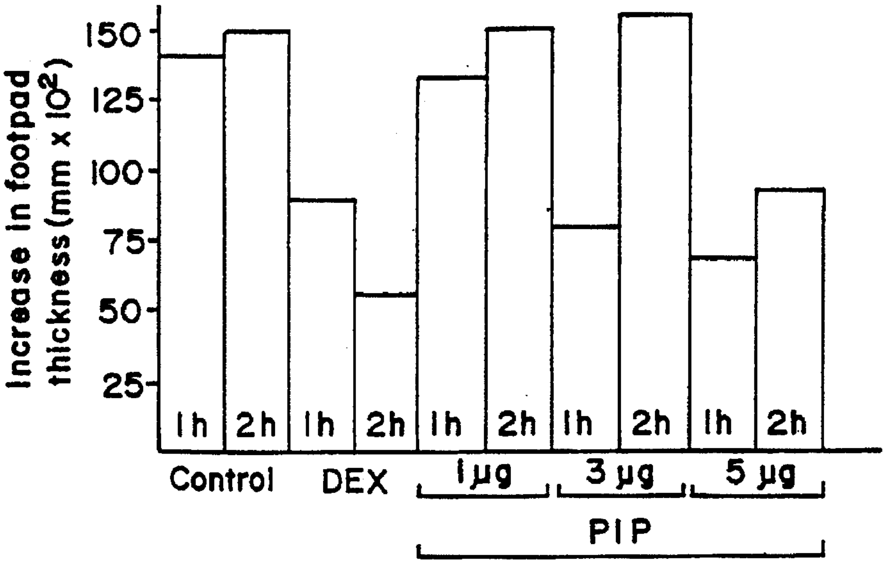
FIG. 20 shows the activity of the hPIP injected simultaneously with carrageenin in an in vivo paw-edema assay.

FIG. 20 shows the results as increase in foot pad thickness (mm×$10^2$) of determinations using 0–5 μg of the purified hPIP, isolated from SDS-PAGE, in experimental injections or 2.5 μg dexamethasone in control injections, each co-administered with the carrageenin. The hPIP significantly reduced the edema in a dose-dependent manner. The control DEX also reduced the inflammation, although the time dependence, as shown in FIG. 20, is slightly different from that of PIP.

Figure 21:
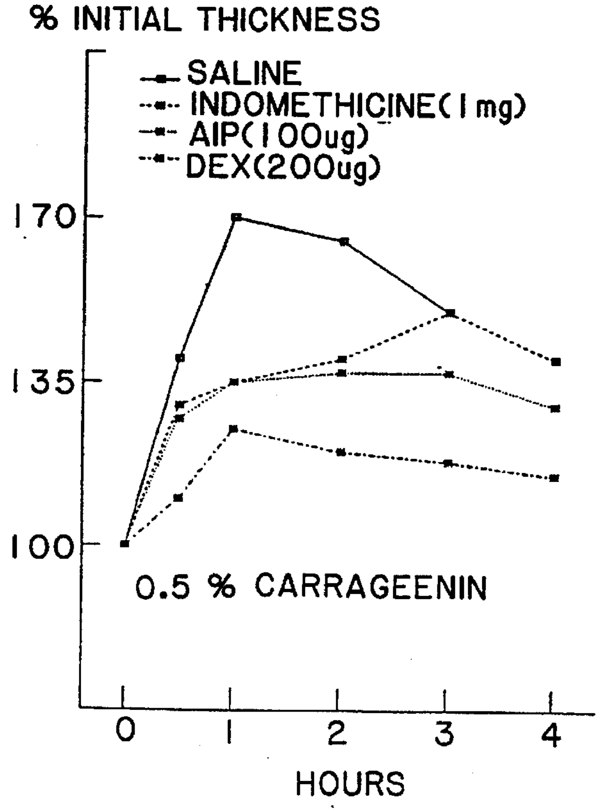
FIG. 21 shows the relative abilities of 100 μg of purified hPIP, 1 mg of indomethacin and 200 μg of dexamethasone to inhibit hind paw edema when administered into the peritoneal cavity.

FIG. 21 shows the results when injection of the test materials was made intraperitoneally 30 min prior to inducing inflammation. Indomethacin as well as DEX was used as a control. The data show that PIP and indomethacin are comparably effective in suppressing paw swelling, although both were slightly less effective than DEX. Accordingly, hPIP is able to enter the circulation and act at the site of inflammation.

Figure 22:
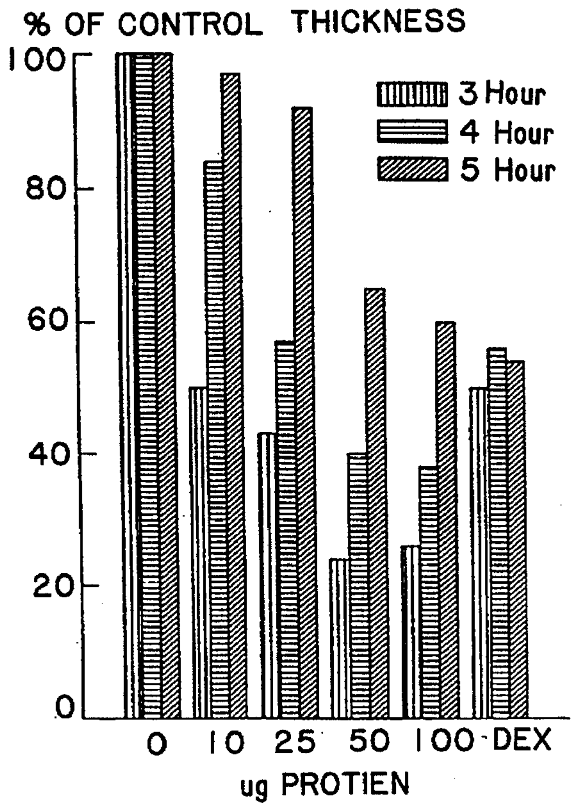
FIG. 22 shows the relative abilities of various doses of the purified hPIP to inhibit hind paw edema when administered to rats via the femoral vein.

FIG. 22 shows the results when administration was made by injection into the femoral vein 2 min prior to the injection of carrageenin. Again, hPIP was effective in inhibiting inflammation over 3, 4, or 5 hr following IV administration in a dose-dependent manner, and 25 μg of PIP were equivalent to the effect of 200 μg DEX after 3 or 4 hr. The results permitted an estimate of the biological half-life of 2–3 hr for PIP.

Figure 23:
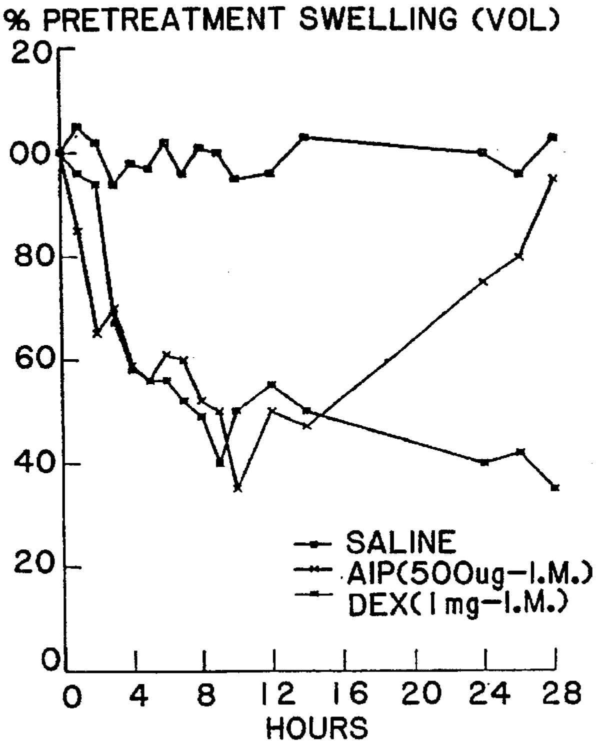
FIG. 23 displays the relative abilities of purified hPIP and dexamethasone (200 μg), when administered to rats intramuscularly, to inhibit joint swelling associated with adjuvant induced arthritis.

The remaining in vivo assay was the adjuvant-induced arthritis model, according to the method of Colpaert, F.C., et al, *Life Sci* (1982) 31:67–75. Thirty days following induction, the animals received intramuscular injections of saline, purified hPIP, or dexamethasone. hPIP, as shown in FIG. 23, was successful in producing a rapid diminution of hind paw and joint swelling which reached a maximum by 10 hr but the swelling returned to control levels after 28 hr. DEX produced swelling reduction after 3 hr, which was maintained for the full 28 hr experimental period.

E. Standard Methods

Most of the techniques which are used to transform cells, construct vectors, extract messenger RNA, prepare cDNA libraries, and the like are widely practiced in the art, and most practitioners are familiar with the standard resource materials which describe specific conditions and procedures. However, for convenience, the following paragraphs may serve as a guideline.

E.1. Hosts and Control Sequences

Both procaryotic and eucaryotic systems may be used to express the PIP encoding sequences; procaryotic hosts are, of course, the most convenient for cloning procedures.

Procaryotes most frequently are represented by various strains of *E. coli*; however, other microbial strains may also be used. Plasmid vectors which contain replication sites and control sequences derived from a species compatible with the host are used; for example, *E. coli* is typically transformed using derivatives of pBR322, a plasmid derived from an *E. coli* species by Bolivar, et al, *Gene* (1977) 2:95. pBR322 contains genes for ampicillin and tetracycline resistance, and thus provides additional markers which can be either retained or destroyed in constructing the desired vector. Commonly used procaryotic control sequences which are defined herein to include promoters for transcription initiation, optionally with an operator, along with ribosome binding site sequences, include such commonly used promoters as the beta-lactamase (penicillinase) and lactose (lac) promoter systems (Chang, et al, *Nature* (1977) 198:1056 and the tryptophan (trp) promoter system (Goeddel, et al *Nucleic Acids Res* (1980) 8:4057 and the lambda derived $P_L$ promoter and N-gene ribosome binding site (Shimatake, et al, *Nature* (1981) 292:128).

In addition to bacteria, eucaryotic microbes, such as yeast, may also be used as hosts. Laboratory strains of *Saccharomyces cerevisiae*, Baker's yeast, are most used although a number of other strains are commonly available. Vectors employing, for example, the 2 μ origin of replication of Broach, J. R., *Meth Enz* (1983) 101:307, or other yeast compatible origins of replications (see, for example, Stinchcomb. et al, *Nature* (1979) 282:39, Tschempe, et al, *Gene* (1980) 10:157 and Clarke, L, et al, *Meth Enz* (1983) 101:300) may be used. Control sequences for yeast vectors include promoters for the synthesis of glycolytic enzymes (Hess, et al, *J Adv Enzyme Reg* (1968) 7:149; Holland, et al, *Biochemistry* (1978) 17:4900). Additional promoters known in the art include the promoter for 3-phosphoglycerate kinase (Hitzeman, et al, *J Biol Chem* (1980) 255:2073), and those for other glycolytic enzymes. Other promoters, which have the additional advantage of transcription controlled by growth conditions are the promoter regions for alcohol dehydrogenase 2, isocytochrome C, acid phosphatase, degradative enzymes associated with nitrogen metabolism, and enzymes responsible for maltose and galactose utilization. It is also believed terminator sequences are desirable at the 3' end of the coding sequences. Such terminators are found in the 3'untranslated region following the coding sequences in yeast-derived genes.

It is also, of course, possible to express genes encoding polypeptides in eucaryotic host cell cultures derived from multicellular organisms. See, for example, Axel, et al, U.S. Pat. No. 4,399,216. These systems have the additional advantage of the ability to splice out introns and thus can be used directly to express genomic fragments. Useful host cell lines include VERO and HeLa cells, and Chinese hamster ovary (CHO) cells. Expression vectors for such cells ordinarily include promoters and control sequences compatible with mammalian cells such as, for example, the commonly used early and late promoters from Simian Virus 40 (SV 40) (Fiers, et al, *Nature* (1978) 273:113), or other vital promoters such as those derived from polyoma, Adenovirus 2, bovine papiloma virus, or avian sarcoma viruses. The controllable promoter, hMT-II (Karin, M., et al, *Nature* (1982) 299:797–802) may also be used. General aspects of mammalian cell host system transformations have been described by Axel (supra). It now appears, also that "enhancer" regions are important in optimizing expression; these are, generally, sequences found upstream or downstream of the promoter region in non-coding DNA regions. Origins of replication may be obtained, if needed, from viral sources. However, integration into the chromosome is a common mechanism for DNA replication in eucaryotes.

E.2. Transformations

Depending on the host cell used, transformation is done using standard techniques appropriate to such cells. The calcium treatment employing calcium chloride, as described by Cohen, S. N., *Proc Natl Acad Sci* (*USA*) (1972) 69:2110, or the $RbCl_2$ method described in Maniatis, T., et al, *Molecular Cloning: A Laboratory Manual* (1982) Cold Spring Harbor Press, p. 254 may be used for procaryotes or other cells which contain substantial cell wall barriers. For mammalian cells without such cell walls, the calcium phosphate precipitation method of Graham and van der Eb, *Virology* (1978) 52:546, optionally as modified by Wigler, M., et al, *Cell* (1979) 16:777–785 may be used. Transformations into yeast may be carried out according to the method of Van Solingen, P., et al, *J Bact* (1977) 130:946 or of Hsiao, C. L., et al, *Proc Natl Acad Sci* (*USA*) (1979) 76:3829.

E.3. Vector Construction

Construction of suitable vectors containing the desired coding and control sequences employs standard ligation and restriction techniques which are well understood in the art. Isolated plasmids, DNA sequences, or synthesized oligonucleotides are cleaved, tailored, and religated in the form desired.

Site specific DNA cleavage is performed by treating with the suitable restriction enzyme (or enzymes) under conditions which are generally understood in the art, and the particulars of which are specified by the manufacturer of these commercially available restriction enzymes. See, e.g., New England Biolabs, Product Catalog. In general, about 1 μg of plasmid or DNA sequence is cleaved by one unit of enzyme in about 20 μl of buffer solution: in the examples herein, typically, an excess of restriction enzyme is used to insure complete digestion of the DNA substrate. Incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in *Methods in Enzymology* (1980) 65:499–560.

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 min at 20° to 25° C. in 50 mM Tris pH 7.6, 50 mM NaCl, 6 mM $MgCl_2$, 6 mM DTT and 5–10 μM dNTPs. The Klenow fragment fills in at 5' sticky ends but chews back protruding 3' single strands, even though the four dNTPs are present. If desired, selective repair can be performed by supplying only one of the, or selected, dNTPs within the limitations dictated by the nature of the sticky ends. After treatment with Klenow, the mixture is extracted with phenol/chloroform and ethanol precipitated. Treatment under appropriate conditions with Sl nuclease or Bal-31 results in hydrolysis of any single-stranded portion.

Synthetic oligonucleotides are prepared by the method of Efimov, V. A., et al (*Nucleic Acids Res* (1982) 6875–6894), and can be prepared using commercially available automated oligonucleotide synthesizers. Kinasing of single strands prior to annealing or for labeling is achieved using an excess, e.g., approximately 10 units of polynucleotide kinase to 1 nmole substrate in the presence of 50 mM Tris, pH 7.6, 10 mM $MgCl_2$, 5 mM dithiothreitol, 1–2 mM ATP, 1.7 pmoles γ32P-ATP (2.9 mCi/mmole), 0.1 mM spermidine, 0.1 mM EDTA.

Ligations are performed in 15–50 μl volumes under the following standard conditions and temperatures: 20 mM Tris-Cl pH 7.5, 10 mM $MgCl_2$, 10 mM DTT, 33 μg/ml BSA, 10 mM-50 mM NaCl, and either 40 μM ATP, 0.01–0.02 (Weiss) units T4 DNA ligase at 0° C. (for "sticky end" ligation) or 1 mM ATP, 0.3–0.6 (Weiss) units T4 DNA ligase at 14° C. (for "blunt end" ligation). Intermolecular "sticky end" ligations are usually performed at 33–100 μg/ml total DNA concentrations (5–100 nM total end concentration). Intermolecular blunt end ligations (usually employing a 10–30 fold molar excess of linkers) are performed at 1 μM total ends concentration.

In vector construction employing "vector fragments", the vector fragment is commonly treated with bacterial alkaline phosphatase (BAP) or calf intestinal alkaline phosphatase (CIP) in order to remove the 5' phosphate and prevent religation of the vector. Digestions are conducted at pH 8 in approximately 150 mM Tris, in the presence of $Na^+$ and $Mg^{+2}$ using about 1 unit of BAP or CIP per μg of vector at 60° for about one hour. In order to recover the nucleic acid fragments, the preparation is extracted with phenol/chloroform and ethanol precipitated. Alternatively, religation can be prevented in vectors which have been double digested by additional restriction enzyme digestion of the unwanted fragments.

For portions of vectors derived from cDNA or genomic DNA which require sequence modifications, site specific primer directed mutagenesis is used. This is conducted using a primer synthetic oligonucleotide complementary to a single stranded phage DNA to be mutagenized except for limited mismatching, representing the desired mutation. Briefly, the synthetic oligonucleotide is used as a primer to direct synthesis of a strand complementary to the phage, and the resulting double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form: 50% will have the original sequence. The resulting plaques are hybridized with kinased synthetic primer at a temperature which permits hybridization of an exact match, but at which the mismatches with the original strand are sufficient to prevent hybridization. Plaques which hybridize with the probe are then picked, cultured, and the DNA recovered.

E.4. Verification of Construction

In the constructions set forth below, correct ligations for plasmid construction are confirmed by first transforming *E. coli* strain MC1061 obtained from Dr. M. Casabadan (Casabadan, M., et al, *J Mol Biol* (1980) 138:179–207) or other suitable host with the ligation mixture. Successful transformants are selected by ampicillin, tetracycline or other antibiotic resistance or using other markers depending on the mode of plasmid construction, as is understood in the art. Plasmids from the transformants are then prepared according to the method of Clewell, D. B., et al, *Proc Natl Acad Sci* (*USA*) (1969) 62:1159, optionally following chloramphenicol amplification (Clewell, D. B., *J Bacteriol* (1972) 110:667). The isolated DNA is analyzed by restriction and/or sequenced by the dideoxy method of Sanger, F., et al, *Proc Natl Acad Sci* (*USA*) (1977) 74:5463 as further described by Messing, et al, *Nucleic Acids Res* (1981) 9:309, or by the method of Maxam, et al, *Methods in Enzymology* (1980) 65:499.

E.5. cDNA or Genomic Library Production

Human genomic libraries are constructed in γ phage as is known in the art. See, e.g., Maniatis, T., et al, *Cell* (1978) 15: 687–701. cDNA libraries can be prepared as described above in γgt11 phage, or double-stranded cDNA synthesized from mRNA isolated using standard techniques can be prepared for insertion into a plasmid vector such as pBR322 using homopolymeric tailing mediated by calf thymus terminal transferase (Sutcliffe, J. G., *Nucleic Acid Res* (1978) 5:2721–2732). First strand cDNA is synthesized by the RNA-dependent DNA polymerase from Avian Myeloblastosis Virus, by priming with oligo (dT) 12–18 on 5 μg mRNA. The RNA template is then liberated from the nascent DNA strand by denaturation at 100° C. for 5 min, followed by chilling on ice. Second strand DNA is synthesized by using the large fragment of DNA polymerase I of *E. coli*, relying on self-priming at the 3'-end of the first strand molecule, thereby forming a double-stranded hairpin DNA. These molecules are blunt-ended at the open-ended termini, and the hairpin loop is cleaved open with Sl nuclease from *Aspergillus oryzae*. Sl nuclease digestion of the double-stranded cDNA takes place in 300 mM NaCl, 30 mM NaOAc, pH 4.5, 3 mM $ZnCl_2$ for 30 min at 37° C. with 600 units enzyme. The cDNA is extracted with phenol:chloroform, and small oligonucleotides are removed by three ethanol precipitations in the presence of ammonium acetate. This is done as follows: a half volume of 7.5M ammonium acetate and two volumes ethanol are added to the cDNA solution, which is precipitated at −70° C. The blunt-ended, double-stranded cDNA is then fractionated by size using gel filtration through a column (0.3×14 cm) Sepharose 4B (Pharmacia Fine Chemicals, Piscataway, N.J.) or by ultracentrifugation in 5–20% glycerol gradient followed by fractionation of the gradient. cDNA roughly greater than the desired length, e.g., 300 base pairs is retained and recovered by precipitation with 70% ethanol. Short (10–30 nucleotides) polymeric tails of deoxycytosine are added to the 3' termini of the cDNA using a reaction containing 0.2M potassium cacodylate, 25 mM Tris, pH 6.9, 2 mM dithiothreitol, 0.5 mM $CoCl_2$, 200 mM cDTP, 400 μg/ml BSA, and 40 units calf thymus terminal deoxynucleotide transferase for 5 min at 22° C. The reaction is extracted with phenol: chloroform, and small oligonucleotides are removed with three ethanol precipitations in the presence of ammonium acetate.

The tailed cDNA is annealed with a host vector such as pBR322 which has been cleaved with, for example, PstI and tailed with oligo dG. In one operable embodiment 2.5 μg pBR322-dG DNA is annealed with the cDNA at a vector concentration of 5 μg/ml, and the hybrids are transferred into *E. coli* MC1061 by the $CaCl_2$-treatment described by Casabadan, M., et al, *Mol Biol* (1980) 138:179–207.

E.6. Probing cDNA or Genomic Libraries cDNA or genomic libraries may be screened if desired using the colony or plaque hybridization procedures. Colonies or plaques are replicated onto duplicate nitrocellulose filter papers (S & S type BA-85) and colonies are allowed to grow at 37° C. for 14–16 hr on L agar containing 15 μg/ml tetracycline. The colonies are lysed with 10% SDS and the DNA is fixed to the filter by sequential treatment for 5 min with 500 mM NaOH/1.5M NaCl, then 0.5M Tris HCl (pH 8.0)/1.5M NaCl followed by 2×standard saline citrate (SSC). Filters are air dried and baked at 80° C. for 2 hr.

For nick-translated probe, the duplicate filters are prehybridized at 42° C. for 16–18 hr with 10 ml per filter of DNA hybridization buffer (50% formamide (40% formamide if reduced stringency), 5×SSC, pH 7.0, 5×Denhardt's solution (polyvinylpyrrolidine, plus Ficoll and bovine serum albumin: 1×=0.02% of each), 50 mM sodium phosphate buffer at pH 7.0, 0.2% SDS, 50 μg/ml yeast tRNA, and 50 μg/ml denatured and sheared salmon sperm DNA).

Samples are hybridized with nick-translated DNA probes at 42° C. for 12–36 hr for homologous species and 37° C. for heterologous species contained in 5 ml of this same DNA hybridization buffer. The filters are washed two times for 30 min, each time at 50° C., in 0.2×SSC, 0.1% SDS for homologous species hybridization, and at 50° C. in 3×SSC, 0.1% SDS for heterologous species hybridization. Filters are air dried and autoradiographed for 1–3 days at −70° C.

For synthetic (15–30 mer) oligonucleotide probes, the duplicate filters are prehybridized at 42° C. for 2–8 hr with 10 ml per filter of oligo-hybridization buffer (6×SSC, 0.1% SDS, 1 mM EDTA, 5×Denhardt's, 0.05% sodium pyrophosphate and 50 μg/ml denatured and sheared salmon sperm DNA).

The samples are hybridized with kinased oligonucleotide probes of 15–30 nucleotides under conditions which depend on the composition of the oligonucleotide. Typical conditions employ a temperature of 30°–42° C. for 24–36 hr with 5 ml/filter of this same oligo-hybridization buffer containing probe. The filters are washed two times for 15 min at 23° C., each time with 6×SSC, 0.1% SDS and 50 mM sodium phosphate buffer at pH 7, then are washed once for 2 min at the calculated hybridization temperature with 6×SSC and 0.1% SDS, air dried, and are autoradiographed at −70° C. for 2 to 3 days.

If the amino acid sequence of the desired protein or nucleotide sequence encoding it in mRNA is known, the DNA for insertion into the host vectors of the invention may be obtained either by synthetic means, or, if vectors containing such sequences are on deposit or available, by cloning such vectors. For synthesis of the coding sequences, alternating sense and anti-sense overlapping single stranded oligonucleotides are prepared, and the alternating sense and anti-sense single stranded portions filled in enzymatically by treating with DNA polymerase and dNTPs. The oligomers are prepared by the method of Efimov, V. A., et al (*Nucleic Acids Res* (1982) 6875–6894), and can be prepared using commercially available automated oligonucleotide synthesizers. Kinasing of single strands prior to annealing or for labeling is achieved using an excess, e.g., approximately 10 units of polynucleotide kinase to 1 nmole substrate in the presence of 50 mM Tris, pH 7.6, 10 mM $MgCl_2$, 5 mM dithiothreitol, 1–2 mM ATP, 1.7 pmoles γ32P-ATP (2.9 mCi/mmole), 0.1 mM spermidine, 0.1 mM EDTA.

E.7. Hosts Exemplified

Host strains used in cloning and expression herein are as follows:

For cloning and sequencing, and for expression of construction under control of most bacterial promoters, *E. coli* strain MC1061 was used.

The cells used for mammalian expression are Chinese hamster ovary (CHO) cells.

We claim:

1. Antibodies which react with an hPIP protein having an amino acid sequence identical to the hPIP amino acid sequence of FIG. 13.

2. Antibodies which react with human phospholipase inhibitory protein/apolipoprotein AIV complex (hPIP/apoAIV), wherein the hPIP/apoAIV complex is purified by the process of (a) treating human interperitoneal dialysis fluid with 40–60% ammonium sulfate to obtain a precipitate;

(b) subjecting the precipitate to Affi-gel to obtain an unbound fraction;

(c) treating the unbound fraction of (b) with concanavalin-A sepharose to obtain an unbound fraction;

(d) subjecting the unbound fraction of (c) to anionic exchange chromatography at pH 7–9 to obtain an active fraction;

(e) treating the active fraction from (d) by preparative SDS-PAGE to obtain a 40 kD fraction; and (f) recovering the 40 kD fraction of (e) wherein the 40 kD fraction comprises a protein having an amino acid sequence identical to the hPIP amino acid Sequence of FIG. 13.

* * * * *